(12) United States Patent
Ortoleva

(10) Patent No.: US 11,468,967 B2
(45) Date of Patent: Oct. 11, 2022

(54) EPITOPE FLUCTUATION AND IMMUNOGENICITY

(75) Inventor: Peter J. Ortoleva, Bloomington, IN (US)

(73) Assignee: INDIANA UNIVERSITY RESEARCH & TECHNOLOGY CORP., Indianapolis, IN (US)

( * ) Notice: Subject to any disclaimer, the term of this patent is extended or adjusted under 35 U.S.C. 154(b) by 1185 days.

(21) Appl. No.: 14/000,788

(22) PCT Filed: Mar. 5, 2012

(86) PCT No.: PCT/US2012/027696
§ 371 (c)(1),
(2), (4) Date: Aug. 21, 2013

(87) PCT Pub. No.: WO2012/122087
PCT Pub. Date: Sep. 13, 2012

(65) Prior Publication Data
US 2013/0332122 A1    Dec. 12, 2013

Related U.S. Application Data

(60) Provisional application No. 61/449,634, filed on Mar. 5, 2011.

(51) Int. Cl.
  *G16B 5/30*    (2019.01)
  *G16B 5/00*    (2019.01)
  *G16B 15/00*   (2019.01)
  *G16B 15/20*   (2019.01)

(52) U.S. Cl.
  CPC ............... *G16B 5/30* (2019.02); *G16B 5/00* (2019.02); *G16B 15/00* (2019.02); *G16B 15/20* (2019.02)

(58) Field of Classification Search
  CPC ... A61K 39/145; G06F 17/5018; G06F 19/12; G06F 19/16
  See application file for complete search history.

(56) References Cited

U.S. PATENT DOCUMENTS

| | | |
|---|---|---|
| 5,553,004 A | 9/1996 | Ronbech-Jensen et al. |
| 6,125,235 A | 9/2000 | Padilla |
| 2002/0009756 A1 | 1/2002 | Mandell et al. |
| 2002/0013687 A1 | 1/2002 | Ortoleva |
| 2004/0091945 A1 | 5/2004 | Fitzer-Attas et al. |
| 2004/0209295 A1* | 10/2004 | Schwabe .......... C07K 14/70539 435/6.14 |

(Continued)

OTHER PUBLICATIONS

Oomen et al., Immunogenicity of Peptide-vaccine Candidates Predicted by Molecular Dynamics Simulations, 2003, Elsevier Science Ltd., pp. 1083-1089.*

Ensing, Hybrid molecular dynamics, Jul. 2010, University of Amsterdam, pp. 1-3.*

(Continued)

*Primary Examiner* — Boris Gorney
*Assistant Examiner* — Bernard E Cothran
(74) *Attorney, Agent, or Firm* — Barnes & Thornburg LLP

(57) ABSTRACT

Systems and methods for computer-aided vaccine design may comprise performing one or more molecular d

(56) References Cited

U.S. PATENT DOCUMENTS

| | | | |
|---|---|---|---|
| 2005/0054197 A1* | 3/2005 | Sato | G06F 17/5018 |
| | | | 438/689 |
| 2005/0136481 A1* | 6/2005 | Trabanino | G06F 19/16 |
| | | | 435/7.1 |
| 2006/0160136 A1 | 7/2006 | Xiang | |
| 2006/0257944 A1 | 11/2006 | Fridman et al. | |
| 2008/0059140 A1 | 3/2008 | Salmon et al. | |
| 2008/0147360 A1 | 6/2008 | Fejes et al. | |
| 2008/0172215 A1 | 7/2008 | Heckerman et al. | |
| 2009/0037159 A1 | 2/2009 | Wen et al. | |
| 2010/0068217 A1* | 3/2010 | Kwong | G06F 19/16 |
| | | | 424/185.1 |
| 2010/0074920 A1 | 3/2010 | Natunen et al. | |
| 2010/0158823 A1* | 6/2010 | Cheng | C07K 14/001 |
| | | | 424/49 |

OTHER PUBLICATIONS

Ensing, Hybrid molecular dynamics, Oct. 21, 2010, University of Amsterdam, pp. 1-6.*

Pacific Immunology, What is an Epitope, 2017, Pacific Immunology, p. 1.*

Schmuck, Molecules with Helical Structure: How To Build a Molecular Spiral Staircase, Wiley-VCH Verlag, 2003, vol. 42, pp. 2448-2452.*

Dictionary.com, Definition of Synthesize, 2017, Dictionary.com, pp. 1-4.*

Ma et al., Molecular dynamics simulations of alanine rich B-sheet oligomers: Insight into amyloid formation, 2002, Cold Spring Harbor Laboratory Press, pp. 2335-2350.*

Tsai, An Introduction to Computational Biochemistry, 2002, John Wiley and Sons, Inc., pp. 1-370 (Year: 2002).*

PCT International Search Report and Written Opinion completed by the ISA/US dated May 21, 2012 and issued in connection with PCT/US2012/027696.

Joshi, et al. "A molecular dynamics study of loop fluctuation in human papillomavrius type 16 virus-like particulars: A possible indicator of immunogenicity" Vaccine: Nov. 28, 2011; vol. 29, No. 51; pp. 9423-9430; abstract.

Tong, et al. "Methods and protocols for prediction of immunogenic epitopes." Briefings in Bioinformatics; Oct. 31, 2006; vol. 8, No. 2; pp. 96-108; esp. Figures 1-3.

Nielsen et al., "Recent progress in adaptive multiscale molecular dynamics simulations of soft matter", Physical Chemistry Chemical Physics, vol. 12, No. 39, Oct. 21, 2010, 15 pages.

PCT International Search Report issued in connection with PCT/US2012/020569 and completed by the U.S. Searching Authority dated Apr. 18, 2012.

Wu et al., "Self-Guided Langevin Dynamics Simulation Method", In Chemical Physics Letters, vol. 381, Issue 3-4, pp. 512-518. Published Nov. 2003.

* cited by examiner

EPITOPE FLUCTUATION AND IMMUNOGENICITY

CROSS-REFERENCE TO RELATED APPLICATIONS

This application is a U.S. national counterpart application of International Application Serial No. PCT/US2012/027696, filed Mar. 5, 2012, which claims the benefit of U.S. Provisional Patent Application No. 61/449,634 filed Mar. 5, 2011. The entire disclosures of both of the foregoing applications are hereby incorporated by reference.

TECHNICAL FIELD

The present disclosure relates generally to the role of epitope fluctuation in immunogenicity. More particularly, the present disclosure relates to the use of epitope fluctuation measurements as part of computer-aided vaccine design methods.

BACKGROUND ART

Vaccines for the prevention of cervical cancer by Human Papillomavirus (HPV) infection have been developed from the capsid of HPV viruses. The vaccine Gardasil®, commercially available from Merck & Co. of Whitehouse Station, N.J., which is effective against four HPV types (HPV6, HPV11, HPV16, HPV18) and has been very successful in preventing HPV infection, is composed of virus-like particles (VLP). Upon vaccination, type-specific antibodies generated by the immune system are capable of neutralizing HPV pathogens. As more than forty HPV infectious types have been identified, a need exists to expand the capabilities of current vaccines to target a broader family of HPV viruses. Vaccine effectiveness is tied to the immunogenicity of VLPs and the production of neutralizing antibodies.

DISCLOSURE OF INVENTION

The present invention may comprise one or more of the features recited in the appended claims and/or one or more of the following features and any combinations thereof.

According to one aspect, a computer-aided vaccine design method may comprise performing one or more molecular dynamics simulations of a protein assembly having at least one epitope, determining a fluctuation measurement for the at least one epitope using the one or more molecular dynamics simulations, and predicting the immunogenicity of the protein assembly in response to the fluctuation measurement. In some embodiments, the protein assembly may be a virus-like particle. In other embodiments, the protein assembly may be a pentamer.

In some embodiments, determining the fluctuation measurement for the at least one epitope may comprise determining a distribution of backbone dihedral angles in conformational space. In other embodiments, determining the fluctuation measurement for the at least one epitope may comprise calculating a root-mean-square deviation of epitope fluctuation. In such embodiments, calculating the root-mean-square deviation of epitope fluctuation may comprise summing fluctuations for each backbone atom during the one or more molecular dynamics simulations and dividing by a total number of backbone atoms.

In other embodiments, determining the fluctuation measurement for the at least one epitope may comprise calculating a correlation matrix between the at least one epitope and other structures in the protein assembly. In still other embodiments, determining the fluctuation measurement for the at least one epitope may comprise analyzing a Fourier spectrum of epitope fluctuation.

In some embodiments, predicting the immunogenicity of the protein assembly in response to the fluctuation measurement may further comprise predicting the immunogenicity of the protein assembly in response to at least one other molecular descriptor of the protein assembly. The one or more molecular dynamics simulations may be performed using a deductive multiscale simulator. The computer-aided vaccine design method may further comprise synthesizing a vaccine comprising the protein assembly.

According to another aspect, one or more computer readable media may comprise a plurality of instructions which, when executed by one or more processors, cause the one or more processors to perform one or more molecular dynamics simulations of a protein assembly having at least one epitope, determine a fluctuation measurement for the at least one epitope using the one or more molecular dynamics simulations, and predict the immunogenicity of the protein assembly in response to the fluctuation measurement. In some embodiments, the protein assembly may be a virus-like particle. In other embodiments, the protein assembly may be a pentamer.

In some embodiments, the plurality of instructions may cause the one or more processors to determine the fluctuation measurement for the at least one epitope, at least in part, by determining a distribution of backbone dihedral angles in conformational space. In other embodiments, the plurality of instructions may cause the one or more processors to determine the fluctuation measurement for the at least one epitope, at least in part, by calculating a root-mean-square deviation of epitope fluctuation. In such embodiments, the plurality of instructions may cause the one or more processors to calculate the root-mean-square deviation of epitope fluctuation by summing fluctuations for each backbone atom during the one or more molecular dynamics simulations and dividing by a total number of backbone atoms.

In other embodiments, the plurality of instructions may cause the one or more processors to determine the fluctuation measurement for the at least one epitope, at least in part, by calculating a correlation matrix between the at least one epitope and other structures in the protein assembly. In still other embodiments, the plurality of instructions may cause the one or more processors to determine the fluctuation measurement for the at least one epitope, at least in part, by analyzing a Fourier spectrum of epitope fluctuation.

In some embodiments, the plurality of instructions may further cause the one or more processors to predict the immunogenicity of the protein assembly in response to at least one other molecular descriptor of the protein assembly. The plurality of instructions may cause the one or more processors to perform the one or more molecular dynamics simulations using a deductive multiscale simulator.

BRIEF DESCRIPTION OF DRAWINGS

The detailed description particularly refers to the accompanying figures in which.

BEST MODE(S) FOR CARRYING OUT THE INVENTION

Figure 1:
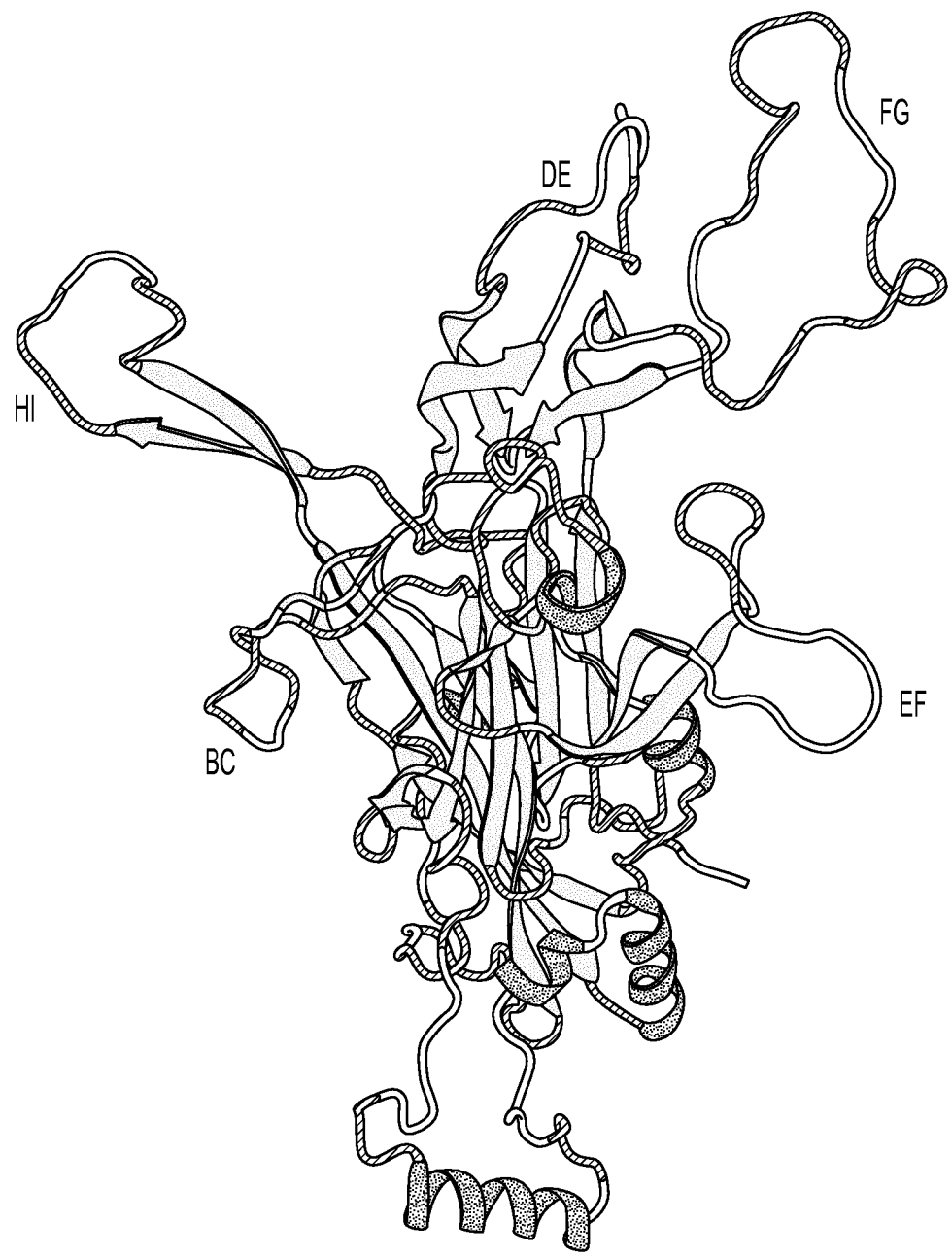
FIG. 1 is a diagram illustrating an all-atom description of the epitope regions of a thermally equilibrated L1 HPV-protein.
Figure 2A:
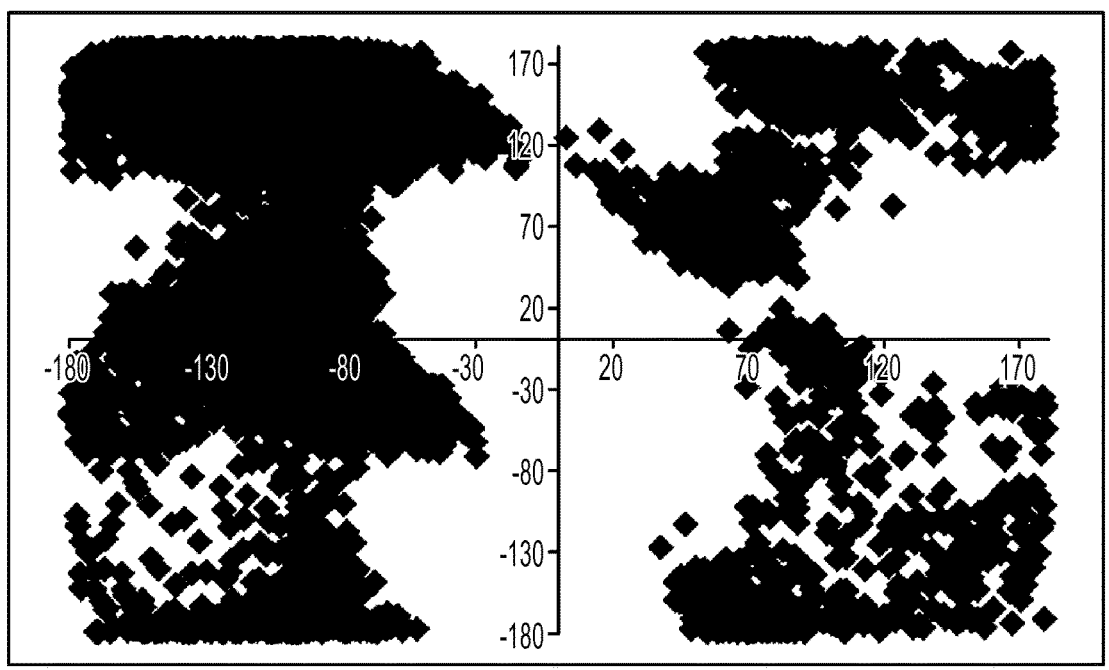
FIG. 2A is a graph illustrating a dihedral distribution for an FG loop in an L1 protein, using a 10 ns trajectory.
Figure 2B:
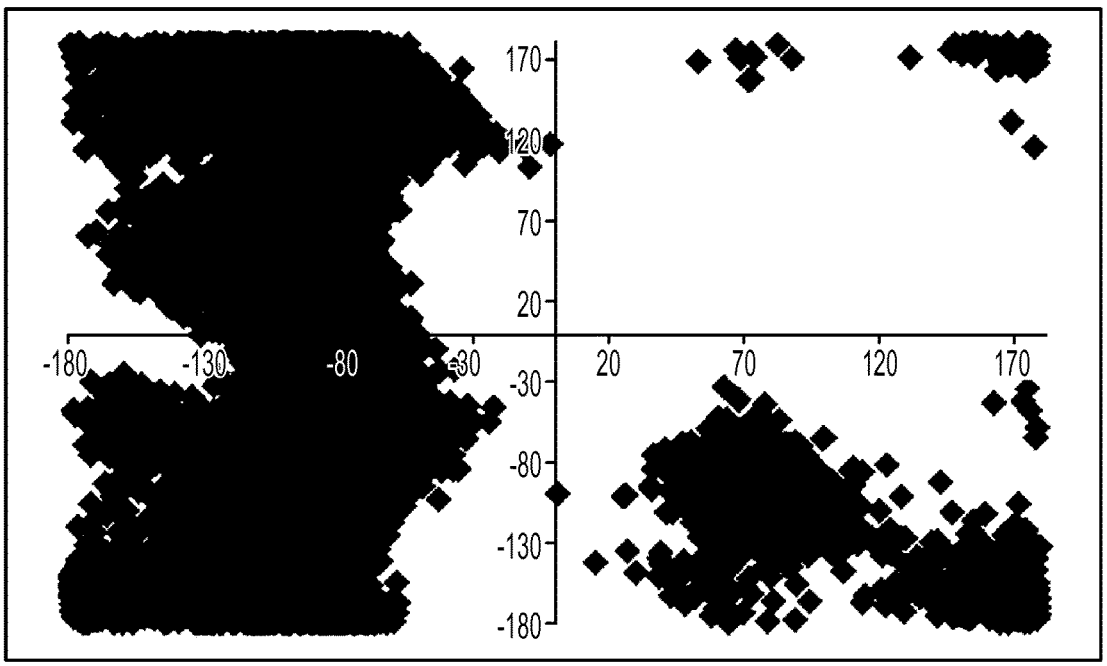
FIG. 2B is a graph illustrating a dihedral distribution for an FG loop in an L1 protein of a pentamer simulation, using an 8 ns trajectory.
Figure 2C:
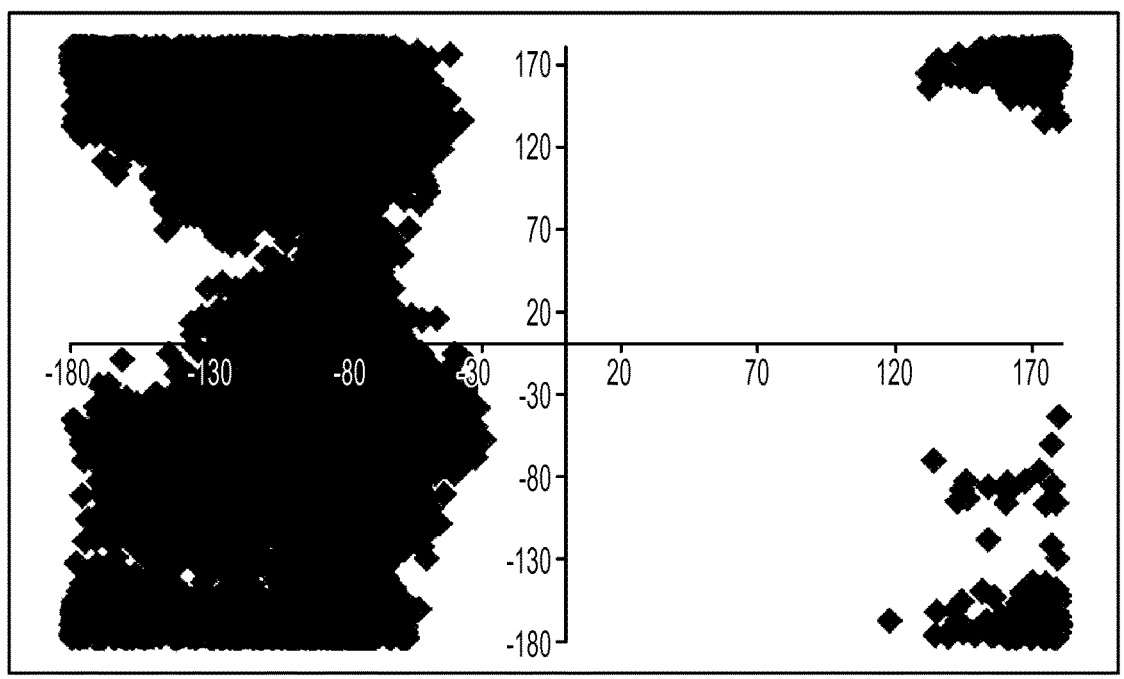
FIG. 2C is a graph illustrating a dihedral distribution for an FG loop in an L1 protein of a VLP simulation, using a 5 ns trajectory.
Figure 3A:
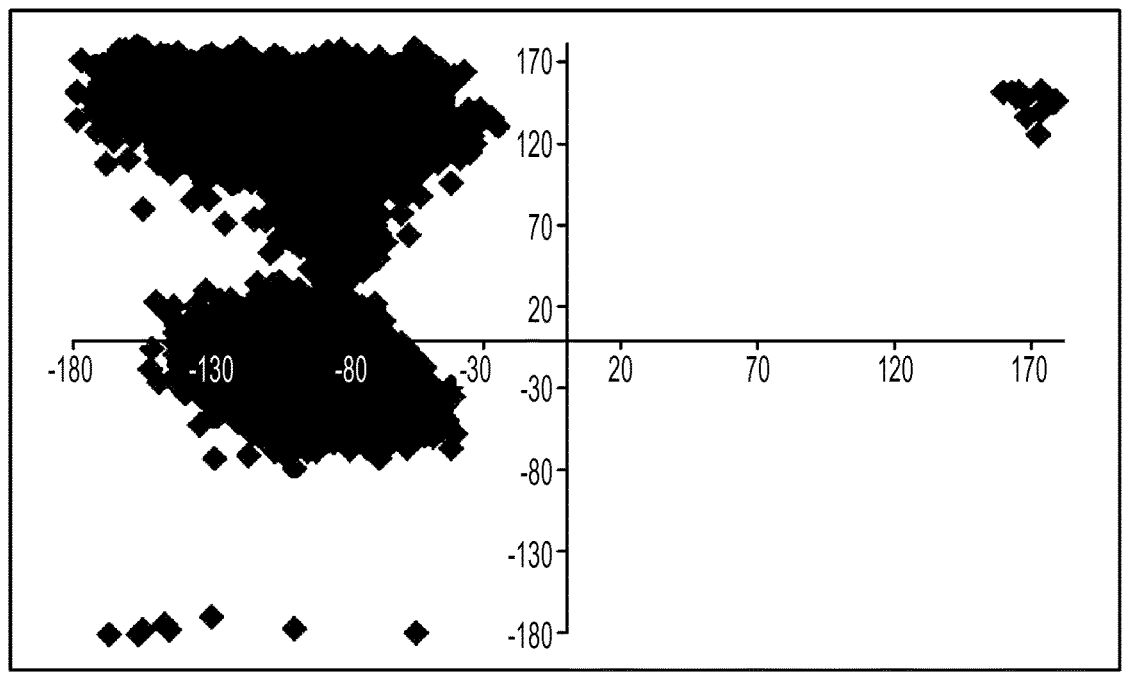
FIG. 3A is a graph illustrating a dihedral distribution for an HI loop in an L1 protein, using a 10 ns trajectory.
Figure 3B:
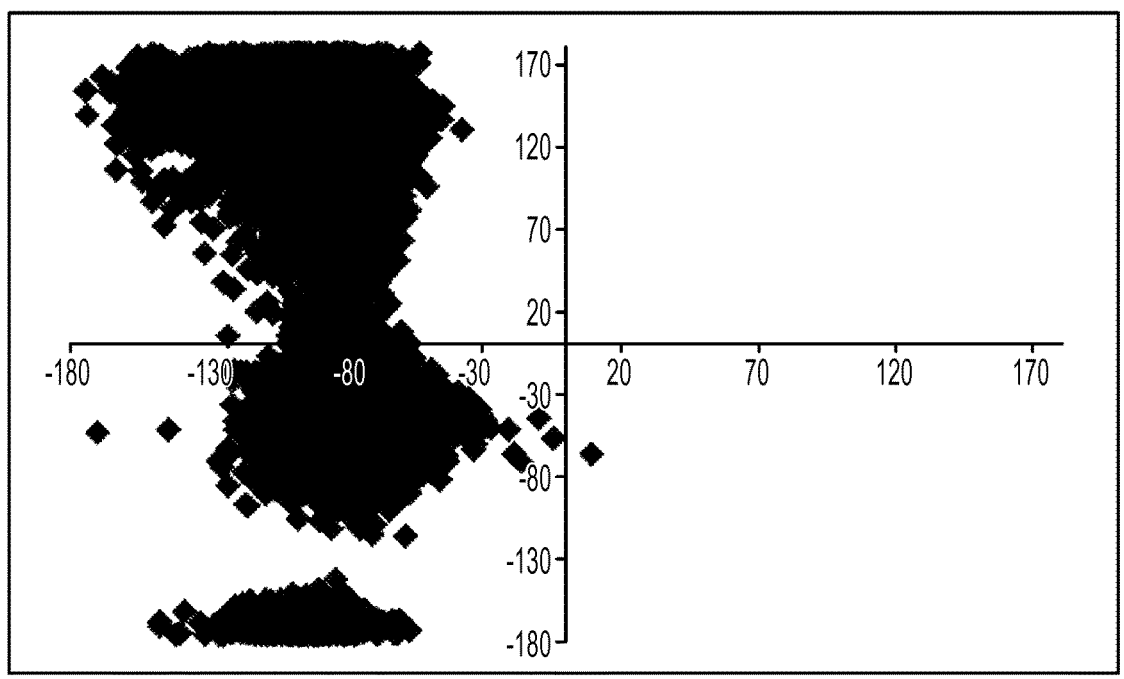
FIG. 3B is a graph illustrating a dihedral distribution for an HI loop in an L1 protein of a pentamer simulation, using an 8 ns trajectory.
Figure 3C:
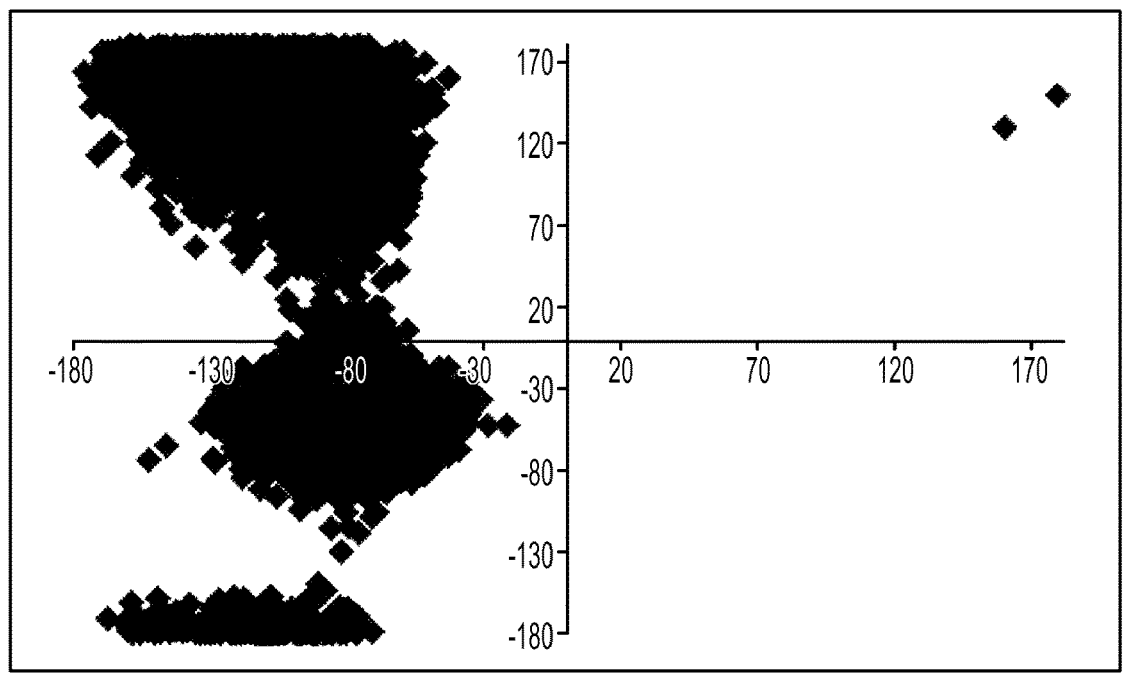
FIG. 3C is a graph illustrating a dihedral distribution for an HI loop in an L1 protein of a VLP simulation, using a 5 ns trajectory.
Figure 4A:
FIG. 4A is a graph illustrating loop fluctuations for an FG loop of a protein.
Figure 4B:
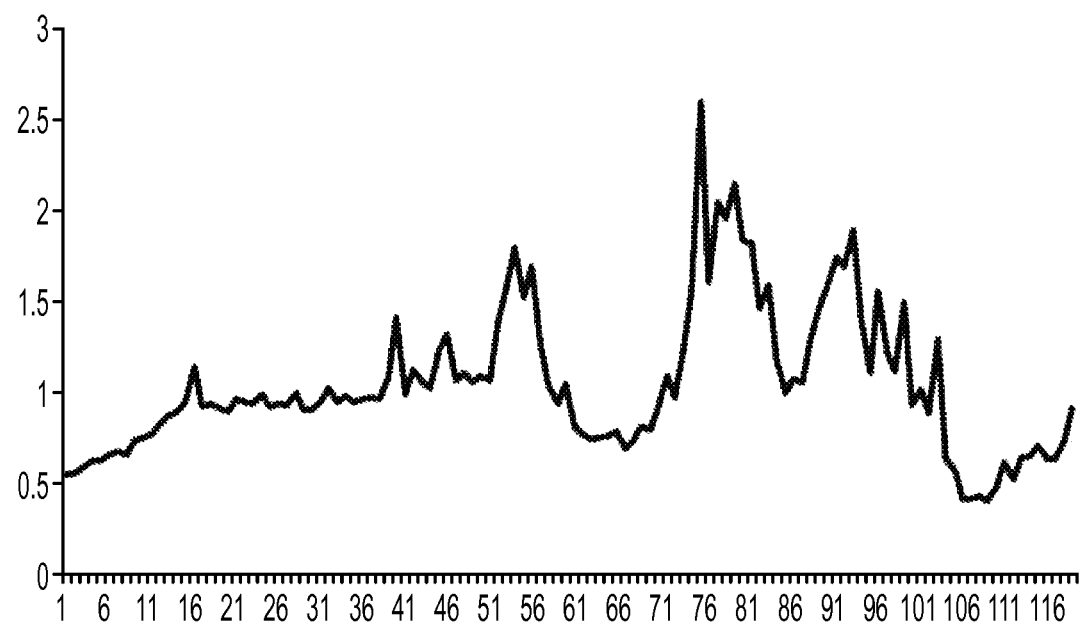
FIG. 4B is a graph illustrating loop fluctuations for an FG loop of a pentamer.
Figure 4C:
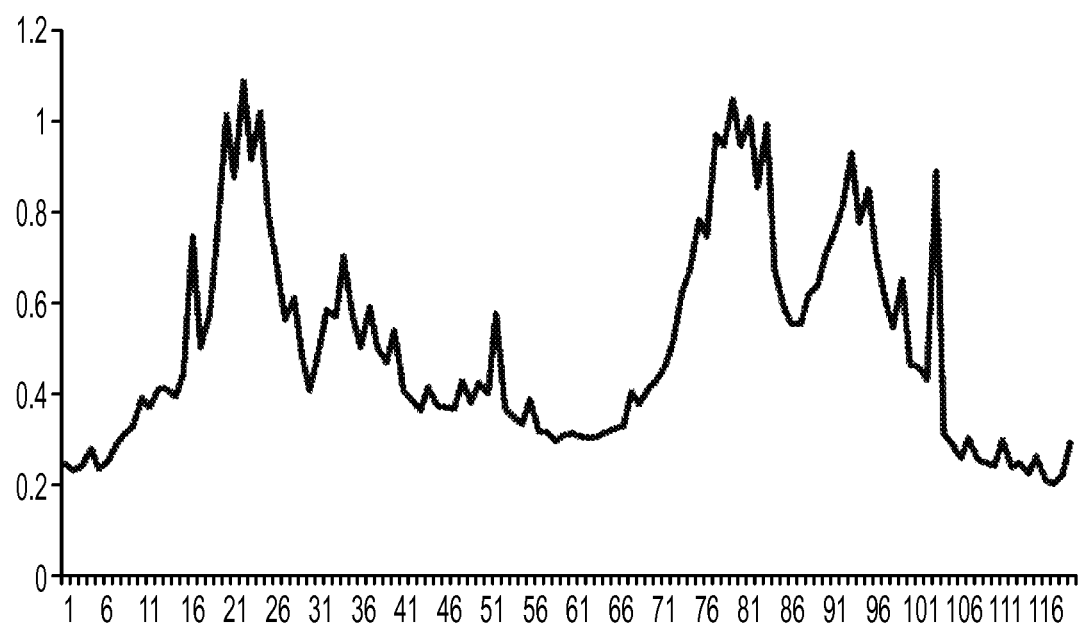
FIG. 4C is a graph illustrating loop fluctuations for an FG loop of a VLP.
Figure 5A:
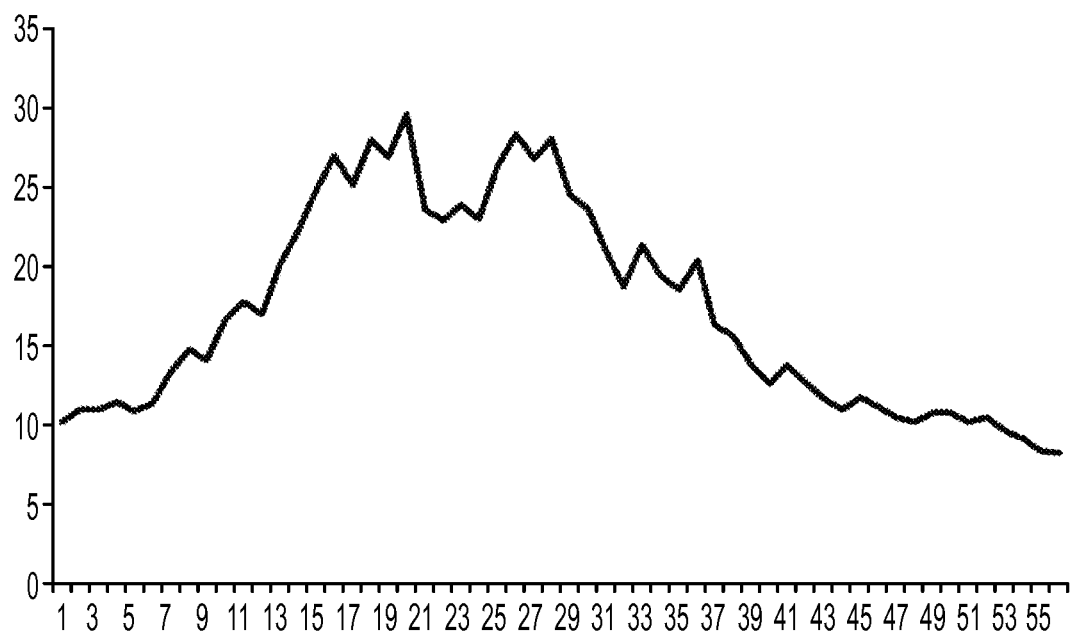
FIG. 5A is a graph illustrating loop fluctuations for an HI loop of a protein.
Figure 5B:
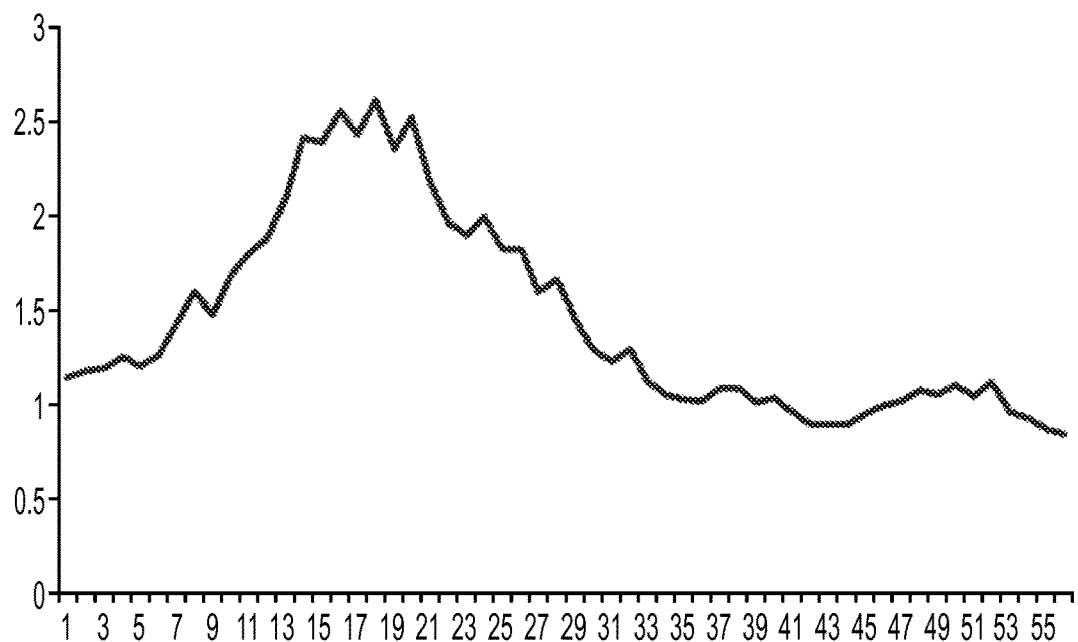
FIG. 5B is a graph illustrating loop fluctuations for an HI loop of a pentamer.
Figure 5C:
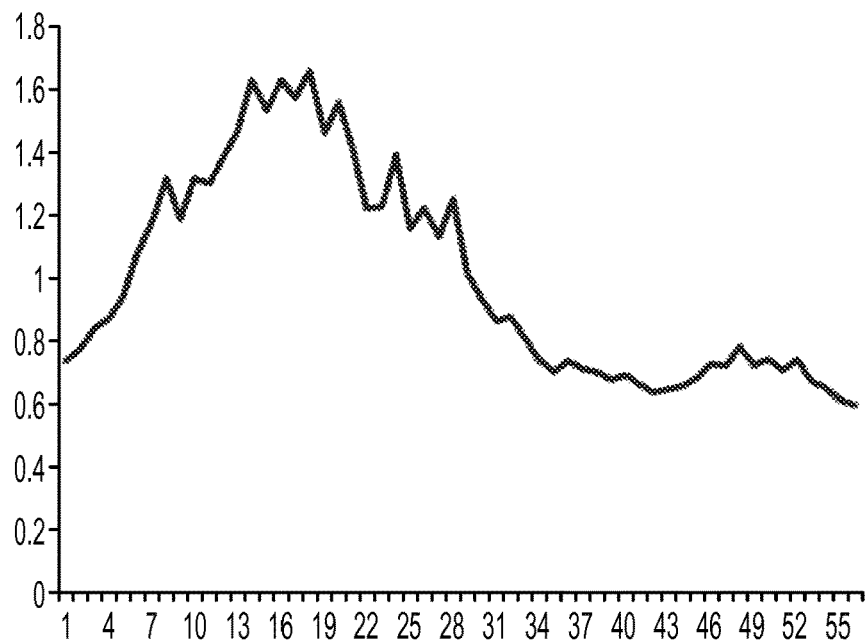
FIG. 5C is a graph illustrating loop fluctuations for an HI loop of a VLP.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and appended claims.

In the following description, numerous specific details may be set forth in order to provide a more thorough understanding of the present disclosure. It will be appreciated, however, by one skilled in the art that embodiments of the invention may be practiced without such specific details. Full software instruction sequences have not been shown in detail in order not to obscure the invention. Those of ordinary skill in the art, with the included descriptions, will be able to implement appropriate functionality without undue experimentation.

References in the specification to "one embodiment," "an embodiment," "an example embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Some embodiments of the invention may be implemented in hardware, firmware, software, or any combination thereof. Embodiments of the invention may be implemented as instructions carried by or stored on one or more machine-readable media, which may be read and executed by one or more processors. A machine-readable medium may be embodied as any device, mechanism, or physical structure for storing or transmitting information in a form readable by a machine (e.g., a computing device). For example, a machine-readable medium may be embodied as read only memory (ROM); random access memory (RAM); magnetic disk storage media; optical storage media; flash memory devices; mini- or micro-SD cards, memory sticks, electrical signals, and others.

According to the present disclosure, a multiscale framework for simulating the dynamics of macromolecules is developed. Their dynamics is divided into high frequency atomic vibrations and slow (coherent) large-spatial-scale conformational changes. A set of OPs is introduced to describe the coherent, overall structural changes while the small amplitude and high frequency atomic fluctuations are described by an equilibrium distribution following from entropy maximization constrained to instantaneous values of the OPs. In effect, OPs as conceived here filter out the high frequency atomistic fluctuations. These concepts are put on a firm mathematical basis via a multiscale analysis of the Liouville equation. The result of the latter analysis is a set of Langevin equations, all factors within which are related to an inter-atomic force-field. This yields a force-field based multiscale algorithm that allows for all-atom simulation of macromolecular structural transitions with high CPU efficiency. This computational approach may be of great value in fundamental and applied studies of the dynamics of macromolecules and their interactions with their microenvironment.

OPs characterize the state of organization of a system. As used herein, OPs describe the overall structure of a macromolecule. The objective of introducing OPs has been dimensionality reduction, i.e., to arrive at a practical computational algorithm for large systems and to understand the salient features of the structure/dynamics of nanoscale assemblies. They are related to the underlying all-atom description, enabling a unified treatment based on the Newtonian Liouville equation. The present disclosure analyzes a set of OPs, showing that they facilitate a complete analysis of macromolecular dynamics.

Given that the OPs evolve much slower than the $10^{-14}$ second timescale of atomistic collisions/vibrations, the latter have sufficient time to arrive at a quasi-equilibrium consistent with the instantaneous state of the OPs. The OPs modify the probability distribution of atomistic configurations which, in turn, determine the diffusions and thermal-average forces mediating OP dynamics. In this view, macromolecular structural dynamics follows from the coupling of processes across multiple scales in space and time. The result of the multiscale analysis of the Newtonian Liouville equation is a set of Langevin equations of stochastic OP dynamics. If the set of OPs is incomplete (i.e., their dynamics is coupled to that of other slowly changing variables) then they satisfy equations involving time delays (i.e., memory effects) as resulting from traditional projection operator analysis. In contrast, the formal multiscale analysis presented here does not involve these memory effects because of the timescale separation enabled by the OPs.

A practical property of macromolecular OPs is that their construction be automatable. This has two implications: (1) the description can readily be enriched if it is found to be incomplete, and (2) the tedious process of inventing new OPs for each macromolecule is avoided. The OPs should capture key features of the free-energy landscape in order to be complete dynamically. In this way, they capture key pathways for structural transitions and associated energy barriers. Earlier choices for OP-like variables include Principal Component Analysis (PCA) modes to identify collective behaviors in macromolecular systems, dihedral angles, curvilinear coordinates to characterize macromolecular folding and coiling, bead models wherein a peptide or nucleotide is represented by a bead which interacts with others via a phenomenological force, and spatial coarse-grained models. These approaches suffer from one or more of the following difficulties: (1) characteristic variables are not slowly varying in time; (2) macromolecular twist is not readily accounted for; (3) their internal dynamics, and hence inelasticity of their collisions is neglected; and (4) the forces involved must be calibrated for most new applications. In contrast, as discussed below, these and other difficulties are overcome in the present approach.

PCA has been successfully used to study protein folding. The PCA modes (involving collective degrees of freedom) probe the global motions of proteins in an "essential" subspace. Dihedral PCA (dPCA) has been suggested to naturally provide a correct separation of internal and overall motions. Free-energy landscapes of several small molecules including protein and RNA hairpin have been analyzed using dPCA. However it has been commented that dPCA produces distortions on the free-energy surface that can lead to artificial energy barriers and minima. One of the simulation methods based on PCA is Essential Dynamics Sampling (EDS). In EDS, the PCA modes are used to guide the macromolecular dynamics. This method has been successfully used to study the folding path of cytochrome c over hundreds of ps, but the principal components vary significantly during large transformations (and, hence, need to be carefully changed from those of the starting structure). Another problem with EDS is the prerequisite of PCA modes that require up to several nanoseconds of Molecular Dynamics (MD) run. For big systems this becomes computationally expensive. Improvements to EDS have been made via a technique called Amplified Collective Motion (ACM). However, normal modes derived from this model via an anisotropic network may not be consistent with all-atom models, especially if the structure undergoes severe deformation. Direct Essential Dynamics (DED), on the other hand, uses the most active collective mode and a weak force to jump out of energy minima. This has been demonstrated on a 15 amino acid S-peptide, where DED trajectories overcome local minima and energy barriers and folded the protein faster than conventional MD. A multidimensional Langevin model of biomolecules, where dPCA modes are used to determine slow, large amplitude motions, has been used to model tri- and hepta-alanine structural transitions. This methodology stresses on the large dimensionality of the model essential for timescale separation. However, to accurately generate the stochastic driving field for the Langevin equation, long time MD data is required to calculate the PCA modes. For example, a 100 ns trajectory is required as an input for subsequent analysis of tri-alanine. "Scrambled" data from replica MD is suggested to suffice. These would again make calculations expensive for large systems that exhibit timescale separation. A variational coarse-graining approach has been used to locate the coarse-grain (CG) sites on centers of masses of various collections of atoms identified via PCA or normal mode analysis based on the $C_\alpha$ atoms of each residue. However, a simulation method has not yet been implemented using this CG representation. In order to account for considerable far-from equilibrium structures, a non-linear dimensionality reduction free-energy profiling scheme based on the isometric mapping algorithm, isomap, has been developed and demonstrated on Src homology 3 protein using MD simulations. Another coarse-graining approach is the rigid region decomposition model. This has been implemented via algorithms like Framework Rigidity Optimized Dynamic Algorithm (FRODA) and Rigid Cluster Normal Mode Analysis (RCNMA) to investigate protein mobility.

According to the present disclosure, the introduction of OPs serves several objectives: (1) providing a set of OPs for macromolecules that capture the essence of macromolecular structural dynamics, (2) providing an efficient computational algorithm to simulate structural dynamics, and (3) demonstrating the applicability of the OPs to a multiscale algorithm via viral RNA simulations. Each of these will be discussed, in turn, below.

A key element of the multiscale analysis of a macromolecule is the identification of OPs that describe its nanoscale features. A central property of an OP is that it evolves slowly. Slow OP dynamics emerges in several ways including inertia associated with the coherent dynamics of many atoms evolving simultaneously, migration over long distances, stochastic forces that tend to cancel, and species population levels as in chemical kinetics or self-assembly which involve many units, only a few of which change on the atomic timescale.

OPs considered here relate macromolecular features to a reference structure (e.g., from X-ray crystallography). The OPs are introduced via (1) a transformation warping space and (2) maximizing their information content to relate them to the atomistic configurations. Consider OPs constructed by embedding the system in a volume $V_S$. Basis functions $U_k(\vec{r})$ for a triplet of labeling indices $\underline{k}$ are introduced. If computations are carried out using periodic boundary conditions to simulate a large system (e.g., to minimize boundary effects and to handle Coulomb forces), periodic basis functions (Fourier modes) can be used. Other possible basis functions would be spherical harmonics when the system is embedded in a spherical volume. More generally, as is familiar in quantum theory or hydrodynamics, the basis functions used are chosen for convenience to reflect the overall geometry of the system and the conditions imposed at the boundary. Furthermore the basis functions should be free of unphysical features (e.g., poles). In one illustrative embodiment, Legendre polynomials were found to be convenient for simulating systems with closed boundaries of rectangular geometry.

In the present disclosure, points $\vec{r}$ within the system are considered to be a displacement of original points $\vec{r}^o$. A set of vector OPs $\vec{\Phi}_{\underline{k}}$ may be constructed as follows. The macromolecule deforms in 3-D space such that a point $\vec{r}$ is displaced from an original point $\vec{r}^o$. Deformation of space taking any $\vec{r}^o$ to $\vec{r}$ is continuous and is used to introduce OPs $\vec{\Phi}_{\underline{k}}$ via $$\vec{r} = \sum_{\underline{k}} U_{\underline{k}}(\vec{r}^o) \vec{\Phi}_{\underline{k}}. \qquad (1)$$

As the $\vec{\Phi}_{\underline{k}}$ change, space is deformed, and so is the macromolecule embedded in it. The objective is to ensure that the dynamics of the $\vec{\Phi}_{\underline{k}}$ reflects the physics of the macromolecule and that the deformation captures key aspects of the atomic-scale details of the structure. In this way, the $\vec{\Phi}_{\underline{k}}$ constitutes a set of vector OPs if they are slowly varying in time.

Let the $i^{th}$ atom in the macromolecule (i=1, . . . N) be moved from its original position $\vec{r}_i^o$ via the above deformation by evolving the $\vec{\Phi}_{\underline{k}}$ and correcting for atomic-scale details as follows. Given a finite truncation of the $\underline{k}$ sum in Eq. (1), for example, choosing $N_{OP}$ number of OPs, there will be some residual displacement (denoted $\vec{\sigma}_i$) for each atom in addition to the coherent deformation generated by the $\underline{k}$ sum:

$$\vec{r}_i = \sum_{\underline{k}} \vec{\Phi}_{\underline{k}} U_{\underline{k}}(\vec{r}_i^o) + \vec{\sigma}_i. \qquad (2)$$

To maximize the information content of the OPs, the magnitude of the $\vec{\sigma}_i$ can be minimized by the choice of basis functions and the number of terms in the $\underline{k}$ sum. Conversely, imposing a permissible size threshold for the residuals allows one to determine the number of terms to include in the $\underline{k}$ sum.

To start the multiscale analysis, the $\vec{\Phi}_{\underline{k}}$ should be expressed in terms of the fundamental variables $\vec{r}_i$. To arrive at this relationship, the mass-weighted square residual $(m_1 \sigma_1^2 + \ldots m_N \sigma_N^2)$ is minimized with respect to the $\vec{\Phi}_{\underline{k}}$ where $m_i$ is the mass of atom i. This implies $$\sum_{\underline{k}'} B_{\underline{k}\underline{k}'} \vec{\Phi}_{\underline{k}'} = \sum_{i=1}^{N} m_i U_{\underline{k}}(\vec{r}_i^o) \vec{r}_i, \quad B_{\underline{k}\underline{k}'} = \sum_{i=1}^{N} m_i U_{\underline{k}}(\vec{r}_i^o) U_{\underline{k}'}(\vec{r}_i^o). \qquad (3)$$

Thus, the OPs can be computed in terms of the atomic positions by solving Eq. (3). For convenience, the basis functions $U_{\underline{k}}$ may be mass weighted orthogonal. In that case, the B-matrix of Eq. (3) is diagonal. $U_{\underline{k}}(\vec{r}_i^o)$ is viewed in this embodiment as the $i^{th}$ component of an N-dimensional vector for an N-atom macromolecule. There are $N_{OP}$ N-dimensional vectors, each labeled by its $\underline{k}$ value. Orthogonalization of these vectors may be carried out using a Gram-Schmidt procedure. In the above notation, $\underline{k}$ is a set of integers (each of which can be 0, 1, . . . ); with this, $\Phi_{100\,X}$ is the X component of the OP $\vec{\Phi}_{100}$ that weights the $U_{100}$ contribution in Eq. (2) after the latter has been subjected to Gram-Schmidt orthogonalization. In this illustrative embodiment, before orthogonalization, $U_{k_1 k_2 k_3}$ is a product of Legendre polynomials of order $k_1$, $k_2$, $k_3$ for the X, Y, Z components of $\vec{r}_i^o$ respectively. The orthogonalization scheme preserves the physical nature of the three fundamental OPs (100X, 010Y, 001Z) because they are chosen to be the first three members of the basis. For other Ops, the $\underline{k}$ labeling corresponds to the original $U_{\underline{k}}(\vec{r}_i^o)$ from which each orthogonal vector was constructed via the Gram-Schmidt procedure.

Mass-weighted orthonormality of the basis functions implies that $B_{kk'}$ is 0 for $k \neq k'$. As such, $$\vec{\Phi}_{\underline{k}} = \frac{\sum_{i=1}^{N} m_i U_{\underline{k}}(\vec{r}_i^o) \vec{r}_i}{\mu_{\underline{k}}}, \quad \mu_{\underline{k}} = \sum_{i=1}^{N} m_i \{U_{\underline{k}}(\vec{r}_i^o)\}^2. \qquad (4)$$

Thus, for a given set of atomic positions the corresponding OPs are uniquely defined.

Next consider the timescale of OP dynamics. The Liouville operator is defined $$L = -\sum_{i=1}^{N} \frac{\vec{p}_i}{m_i} \cdot \frac{\partial}{\partial \vec{r}_i} + \vec{F}_i \cdot \frac{\partial}{\partial \vec{p}_i},$$

where $\vec{p}_i$ and $\vec{F}_i$ are the momentum of, and net force on atom i. Given Eq. (4), one may compute $$\frac{d\underline{\Phi}}{dt} \text{ as } -L\underline{\Phi},$$

where $\underline{\Phi}(\Gamma)$ is a set of OPs $\vec{\Phi}_{\underline{k}}$.

$$\frac{d\vec{\Phi}_{\underline{k}}}{dt} = \frac{\vec{\Pi}_{\underline{k}}}{\tilde{\mu}_{\underline{k}}}, \vec{\Pi}_{\underline{k}} = \sum_{i=1}^{N} U_{\underline{k}}(\vec{r}_i^o)\vec{p}_i. \quad (5)$$

Inclusion of $m_i$ in developing Eq. (3) gives $\vec{\Phi}_{\underline{k}}$ the character of a generalized center-of-mass-like (CM) variable. In fact, if $U_{\underline{k}}$ is a constant then $\vec{\Phi}_{\underline{k}}$ is proportional to the CM. While the $\vec{\Phi}_{\underline{k}}$ are given in terms of a sum of N-atomic displacements, many terms of which have similar directions due to the smooth variation of $U_{\underline{k}}$ with respect to $\vec{r}_i^o$, the momenta $\Pi_{\underline{k}}$ are given by a sum of atomic momenta, which tend to cancel near equilibrium. Hence the thermal average of $\Pi_{\underline{k}}$ is small, and thus the $\vec{\Phi}_{\underline{k}}$ tend to evolve slowly.

Consider the dynamics of the CM, i.e., $\vec{\Phi}_{000}$. From Eq. (5), $\vec{\Phi}_{000}$ satisfies $$\frac{d\vec{\Phi}_{000}}{dt} = \frac{\vec{\Pi}_{000}}{M},$$

where $\tilde{\mu}_{000} = M$ is the total mass of the macromolecule. Since M is large, $\vec{\Phi}_{000}$ evolves slowly relative to the timescale of atomic collision/vibration. This suggests that $\vec{\Phi}_{000}$ satisfies a key criterion to be an OP and serves as the starting point of a multiscale analysis.

To reveal the timescale on which the OPs evolve, it is convenient to define the smallness parameter $\varepsilon = m/M$, where m is a typical atomic mass. For any of the $\vec{\Phi}_{\underline{k}}$, letting $\vec{v}_i$ be the velocity of particle i, the definition of $\varepsilon$ and Eq. (5) yields $$\frac{d\vec{\Phi}_{\underline{k}}}{dt} = \frac{\sum_{i=1}^{N} U_{\underline{k}}(\vec{r}_i^o)\vec{p}_i}{\tilde{\mu}_{\underline{k}}} = \quad (6)$$

$$\frac{\sum_{i=1}^{N} U_{\underline{k}}(\vec{r}_i^o)m_i\vec{v}_i}{\tilde{\mu}_{\underline{k}}} = \frac{\sum_{i=1}^{N} U_{\underline{k}}(\vec{r}_i^o)m\hat{m}_i\vec{v}_i}{M\mu_{\underline{k}}} = \varepsilon \frac{\sum_{i=1}^{N} U_{\underline{k}}(\vec{r}_i^o)\hat{m}_i\vec{v}_i}{\mu_{\underline{k}}} = \varepsilon \frac{\Pi_{\underline{k}}}{\mu_{\underline{k}}},$$

where $\mu_{\underline{k}} = \tilde{\mu}_{\underline{k}}/M$ and $\hat{m}_i = m_i/m$.

Thus, $\vec{\Phi}_{\underline{k}}$ changes at a rate $O(\varepsilon)$ under the assumption that the atomic momenta tend to cancel, as is consistent with the quasi-equilibrium probability distribution $\hat{\rho}$ below. Special initial conditions could make the rate of OP change scale differently; examples of such conditions include an initial density discontinuity (leading to a shockwave), injection of the macromolecule at a high velocity, or a sudden jump in temperature. Under these conditions the slowness of motion within our reduced dimensionality framework (OPs) and all the resulting advantages (e.g., calculating thermal-average forces) is lost. Therefore for any class of initial conditions, the slow rate of OP dynamics should be confirmed before applying the multiscale ideas developed below. The present disclosure demonstrates the applicability of the $\varepsilon$-scaling for typical conditions underlying macromolecular behavior.

A simple case of the $\vec{r}_i$, $\vec{\Phi}_{\underline{k}}$ relationship suggests how it captures rigid rotation. Take $U_{\underline{k}}$, $\underline{k}$=100,010,001 to be $x^o$, $y^o$ and $z^o$ respectively. Neglecting the residuals, Eq. (2) becomes $x_i = \Phi_{100x} x_i^o + \Phi_{010x} y_i^o + \Phi_{001x} z_i^o$, and similar for $y_i$ and $z_i$ (where $x_i$, $y_i$, $z_i$ are the three Cartesian components of $\vec{r}_i$ vector). The relationship can be written in the tensorial form $\vec{r}_i = \overline{\Phi}\vec{r}_i^o$. It is seen that for a special case (i.e., where the tensor $\overline{\Phi}$ is a rotation matrix), $\vec{\Phi}_{\underline{k}}$ constitute a length preserving rotation about the CM if $\vec{r}_i$ is relative to the CM. More generally, for the above three basis functions, the $\vec{r}_i$–$\vec{\Phi}_{\underline{k}}$ relationship corresponds to a mixed rotation, extension/compression. In fact, the OPs defined here constitute a strain tensor thereby accounting for elastic deformations. In addition, the presently disclosed multiscale formulation is all-atom and, hence, captures internal friction effects via the force-field. The theory accounts for both elastic and viscous effects. The higher order OPs (specifically second and third order) capture twisting, bending, and more complex deformations. Such OPs capture polyalanine folding from a linear to a globular state. The Ops also capture nucleation and front propagation in a virus capsid. While it is not trivial to interpret all the deformations associated with the higher order polynomial-defined OPs, it is the generality of the presently disclosed multiscale approach that accounts for all their dynamics. Ultimately the interpretation of the OPs is embodied in the description of the phenomenon itself, e.g., macromolecular structural transition. A commonplace example is hydrodynamics wherein one does not always interpret the meaning of each Fourier density mode, but rather speaks in terms of phenomena such as propagating waves or viscous boundary layers. Additional properties of the OPs are discussed below in Appendix A.

The set $\underline{\Phi}$ of OPs have technical advantages that greatly facilitate theoretical analyses. Consider an extended set $\underline{\Phi}_{ex}$ of OP and OP-like variables, notably the $\vec{\Phi}_{\underline{k}}$ for $\underline{k}$ in the list of OPs plus similarly defined variables $\vec{\Phi}_{\underline{k}res}$ for $\underline{k}$ not in the OP list. Thus, $$\vec{r}_i = \sum_{\underline{k}}^{OP} \vec{\Phi}_{\underline{k}} U_{\underline{k}}(\vec{r}_i^o) + \sum_{\underline{k}}^{res} \vec{\Phi}_{\underline{k}res} U_{\underline{k}}(\vec{r}_i^o). \quad (7)$$

This relation maps the 3N configuration variables $\underline{r}$ onto $\underline{\Phi}_{ex}$, also a 3N-dimensional space. Eq. (7) for $\vec{r}_i$ in terms of $\underline{\Phi}$ and $\underline{\Phi}_{res}$ provides a way to generate ensembles of $\vec{\Phi}_{\underline{k}}$-constrained configurations by randomly varying the $\vec{\Phi}_{\underline{k}res}$. An expression for $\vec{\sigma}_i$ in terms of $\underline{\Phi}_{res}$ is obtained by comparing Eq. (2) and Eq. (7). However, generating ensembles by randomly varying the $\vec{\sigma}_i$ typically leads to very high-energy configurations. This difficulty is readily avoided as long as $\vec{\sigma}_i$ is chosen by constraining $\vec{\Phi}_{\underline{k}res}$ for higher order $\underline{k}$ to small values. The lower $\underline{k}$–$\vec{\Phi}_{\underline{k}res}$ do provide major structural variations by moving atoms in the ensemble with a measure of coherence, avoiding near-atom overlap. Thus, $\vec{\Phi}_{\underline{k}res}$ provides a way to generate rich ensembles at fixed $\underline{\Phi}$ and with modest energies (and, hence, Boltzmann relevance). In practice a "hybrid" sampling method, wherein short MD runs are performed starting with configurations from the $\overline{\Phi}_{k\text{res}}$-generated sample, is used to enrich fluctuations about the constant set of Ops $\underline{\Phi}$. All these properties are important for the practical implementation of a multiscale Molecular Dynamics/Order Parameter extrapolation (MD/OPX) approach and a fully self-consistent multiscale approach and software. Implementation of the former is based on the philosophy of Equation-Free Multiscale (EFM) approach. The absence of macroscopic equations of motion is overcome by extrapolating OPs over large time intervals using short bursts of MD simulation. In contrast, software computations are guided by the Langevin equation for OPs (further described below). The software development is closer to the theme of the Heterogeneous Multiscale Modeling (HMM), in the sense that maximum knowledge (or ignorance) on the various scales in the system is utilized in deriving the quasi-equilibrium probability density.

It should be noted that, even though the OPs are defined in terms of atoms in the macromolecule, the multiscale analysis developed below accounts for both the macromolecule and the medium, allowing simulation of the entire system. Since the OPs evolve on a long timescale, their dynamics filters out the high frequency atomistic fluctuations (residuals). The slowly evolving OPs can be projected over large intervals in time. These timesteps are appreciably larger than simple MD timesteps and, therefore, efficiently probe the long time behavior of a macromolecule. As the above OPs are generated in an automated fashion, the set may be expanded by increasing the range of the $\underline{k}$ sum. As further discussed below, this addresses the difficulty that arises when a limited set of OPs couples to other slow variables.

The OPs considered above and the Liouville equation may be used to derive equations for the stochastic dynamics of a macromolecule. The analysis starts by writing the Liouville equation for the N-atom probability density $\mathcal{Y}$, i.e., $\partial \mathcal{Y}/\partial t = L\mathcal{Y}$ for Liouville operator L. $\mathcal{Y}$ depends on the set of 6N positions and momenta $\Gamma$ and time t.

Multiscale analysis starts with a transformation of the N-atom probability density from the $\mathcal{Y}$ ($\Gamma$,t) formulation to one that makes the multiple ways on which $\mathcal{Y}$ depends on $\gamma$,t more explicit. This involves introduction of a set of OPs $\underline{\Phi}(\Gamma)$ (i.e., $\overline{\Phi}_k$ of Sect. II for all $\underline{k}$ on the list of OPs) that depends on $\Gamma$ and that are shown to evolve on a timescale much greater than that of individual atomic collisions/vibrations.

First, $\mathcal{Y}$ may be written in a form that makes the dependence on $\Gamma$ and t of various types explicit:

$$\mathcal{Y}(\Gamma,t) = \rho\{\Gamma_0(\Gamma),\underline{\Phi}(\Gamma),t_0(t),\underline{t}(t);\varepsilon\}. \tag{8}$$

This makes an ansatz that reformulated probability density $\rho$ depends on the N-atom state $\Gamma$ both directly (i.e., via $\Gamma_0(\Gamma)=\Gamma$) and, via a set of OPs $\underline{\Phi}(\Gamma)$, indirectly. Similarly, $\rho$ depends on the sequence of times $t_0(t)$, $t_1(t)$, $t_2(t)$, ... $=t_0(t)$, $\underline{t}(t)$, where $t_n(t)=\varepsilon^n t$. The times $t_n$ for n>0 are introduced to account for the slower behaviors in $\rho$; while $t_0$ accounts for processes on the fast timescale (i.e., $t_0$ changes by one unit when $10^{-14}$ seconds elapse). $\varepsilon$ is a small parameter, as defined above. The $\varepsilon$ dependence of $\rho$ and scaling of time are justified below.

In adopting this perspective, $\underline{\Phi}$ is not a set of additional independent dynamical variables; rather, its appearance in $\rho$ is a place-holder for a special dependence of $\rho$ on $\Gamma$ that underlies the slow temporal dynamics of $\rho$. A simple example that elucidates the ansatz is the function $f(x)=\exp^{-\varepsilon x}\sin(x)$. $f(x)$ may be restated as $f(x_0, x_1)$, where $x_0=x$ and $x_1=\varepsilon x$. This transformation does not add any independent variable to the description; rather, it makes the discrete dependencies on x explicit. It is shown below that the dual dependence of $\rho$ on $\Gamma$ can be constructed if $\varepsilon$ is sufficiently small. An equation of stochastic OP dynamics that preserves the feedback between the atomistic and nanoscale variables is now obtained via a multiscale perturbation analysis for a classical N-atom system.

The above framework may be used to derive an equation for the OP probability distribution. One finds that $L\Phi$ naturally reveals a small parameter $\varepsilon$ (as described above). Starting with Eq. (8), the Liouville equation for $\mathcal{Y}$ and the chain rule, one obtains the multiscale Liouville equation:

$$\sum_{n=0}^{\infty} \varepsilon^n \partial \rho / \partial t_n = (L_0 + \varepsilon L_1)\rho. \tag{9}$$

Eq. (9) may be solved perturbatively via a Taylor expansion in $\varepsilon$. As shown below in Appendix B, $L_0$ involves partial derivatives with respect to $\Gamma_0$ at constant $\underline{\Phi}$ (when operating on $\rho$ in the multiscale form, Eq. (8)), and conversely for $L_1$. As such, $L_0$ and $L_1$ take the forms:

$$L_0 = -\sum_{i=1}^{N} \frac{\vec{p}_i}{m_i} \Box \frac{\partial}{\partial \vec{r}_i} + \vec{F}_i \Box \frac{\partial}{\partial \vec{p}_i} \tag{10}$$

$$L_1 = -\sum_{\underline{k}} \frac{\Pi}{\mu_k} \Box \frac{\partial}{\partial \underline{\Phi}}. \tag{11}$$

Note that $L_0$ and $L_1$ operate in the space of functions that depend explicitly on variables $\Gamma_0$ and $\underline{\Phi}$; $\underline{\Pi}$ signifies a set of $\Pi_k$ and subscripts 0 on $\vec{r}_i$ and $\vec{p}_i$ in Eq. (10) are henceforth dropped because of the simple $\Gamma_0(\Gamma)=\Gamma$ dependence of $\rho$. While the space of functions on which $L_0$ and $L_1$ operates is composed of $6N+N_{OP}$ variables (the 6N atomic positions and momenta $\Gamma_0$, plus the $N_{OP}$ OPs $\underline{\Phi}$), the formalism does not assume that the variables are dynamically independent. Rather, from Eq. (9) one determines the dependence of $\rho$ on $\Gamma_0$ and $\underline{\Phi}$, but ultimately through Eq. (8) how $\mathcal{Y}$ depends on $\Gamma$. Hence, Eqs. (9)-(11) do not imply that $\Gamma_0$ and $\underline{\Phi}$ are independent dynamical variables but, in accordance with Eq. (8), the equations track the multiple space and time dependencies of $\mathcal{Y}$. There are still 6N dynamical variables, as the OPs do not evolve independently of the 6N atomic positions and momenta. Eq. (4) and Eq. (6) show the explicit dependencies of atomic and coarse-grained quantities. In contrast, one could introduce collective modes as new dynamical variables in addition to the 6N atomic positions and momenta $\Gamma$. However, this approach carries the burden of eliminating selective position and momentum variables to keep the number (6N) of degrees of freedom fixed. In summary, to uncloak the explicit space-time dependencies of the N-particle density $\mathcal{Y}$, $6N+N_{OP}$ variables are used, of which $N_{OP}$ are not independent of the remainder (with dependencies defined via Eq. (4) and Eq. (6)). As no additional independent variables are added to the description of the N-atom system, $\mathcal{Y}$ still remains a function of the 6N dynamical variables. Furthermore, the $O(\varepsilon)$ scaling of the Liouville equation is a natural consequence of the slowness of OPs. This justifies a perturbative solution and hence the ε dependence of the N-atom probability density. With this, the N-atom probability density may be constructed as $$\rho = \sum_{n=0}^{\infty} \varepsilon^n \rho_n.$$

Putting the perturbation expansion for ρ into Eq. (9), and analyzing different orders in ε, the Smoluchowski equation for the coarse-grained probability distribution $\tilde{W}$ is obtained:

$$\frac{\partial \tilde{W}}{\partial \tau} = \sum_{\underline{kk'}} \frac{\partial}{\partial \vec{\Phi}_k} \left[ \vec{\overline{D}}_{\underline{kk'}} \cdot \left[ \frac{\partial}{\partial \vec{\Phi}_{k'}} - \beta \vec{f}_{k'} \right] \tilde{W} \right]. \quad (12)$$

The diffusivity diffusivity factors $\overline{D}_{kk'}$ are related to the correlation function of time derivatives of OPs via:

$$\vec{\overline{D}}_{\underline{kk'}} = \frac{1}{\mu_k \mu_{k'}} \int_{-\infty}^{0} dt'_0 \langle \Pi_k e^{-L_0 t'_0} \Pi_{k'} \rangle, \quad (13)$$

where $\Pi_k$ is defined in terms of the OP time derivatives via Eq. (5) and Eq. (6). In constructing the correlation functions, the initial data is at fixed $\underline{\Phi}$; since $\underline{\Phi}$ does not change appreciably during the period in which the correlation function is appreciable, $\overline{D}_{kk'}$ depends on $\underline{\Phi}$.

The thermal-average force $\vec{f}_k$ is given by $$\vec{f}_k = -\frac{\partial F}{\partial \vec{\Phi}_k} = \langle \vec{f}_k^{m*} \rangle \quad (14)$$

for $\underline{\Phi}$ constrained Helmholtz free-energy F, where $$F = -1/\beta \ln Q(\underline{\Phi}, \beta), \quad (15)$$

$Q(\underline{\Phi}, \beta)$ is the partition function associated with $\hat{\rho}$, and $$\vec{f}_k^{m*} = \sum_{i=1}^{N} U_{\underline{k}}(\vec{r}_i^o) \vec{F}_i^*$$

is the "OP force." Details of the derivation of Eq. (15) derivation are provided below in Appendix C.

Equivalent to Eq. (12) is an ensemble of OP time courses generated by the Langevin equations $$\frac{\partial \vec{\Phi}_k}{\partial \tau} = \beta \sum_{k'} \left[ \vec{\overline{D}}_{\underline{kk'}}, \vec{f}_{k'} \right] + \vec{\xi}_k. \quad (16)$$

The coherent part of the evolution is determined by the product of the diffusion factors and the thermal-average forces; the stochastic evolution is determined by the random force $\vec{\xi}_k$. The latter is constrained by requiring the integral of its auto-correlation function to be proportional to the diffusion coefficient.

The expression for diffusion factors provided above involves an integration of the correlation function over all time. However, if the correlation function decays on a long timescale (i.e., on that comparable to OP evolution), the above Smoluchowski equation would be replaced by one that is non-local in time. This would suggest that the set of OPs couples to other slow variables. Since the OPs are generated automatically (as described above), new slow variables can be added in a straightforward way to make the existing set $\underline{\Phi}$ complete (e.g., eliminate the long-time tail). Completing the set of OPs modifies the operator $L_0$ (and hence the velocity correlation of Eq. (13)), as the latter involves derivatives with respect to $\Gamma_0$ at constant $\underline{\Phi}$. This modifies the diffusion factor, affecting dynamics of the OPs on the free-energy surface they define. Such an operator is automatically accounted for via standard MD codes when the correlation time of OP velocities is short relative to the timescale of OP evolution. Thus, the long-time behavior of correlation functions provides a completeness criterion for the set of OPs and, thereby, a self-consistency check for the theory and computations.

Another self-consistency check is related to refreshing of the reference structure $\underline{r}^0$. In the illustrative embodiment, simulations begin with the energy-minimized and thermally equilibrated X-ray crystallographic or other all-atom structure as the reference structure. As the system evolves in time, the resulting deformation may increase some of the residuals. This may reflect the need for a new reference structure. The reference structure transition point is chosen when the maximum residual for a structure in the constant OP ensemble becomes comparable with its root mean square deviation (RMSD) from the initial reference structure $$\left[ \frac{|\vec{r}_1 - \vec{r}_1^o|^2 + \ldots |\vec{r}_N - \vec{r}_N^o|^2}{N} \right]^{1/2}$$

(i.e., when some local change in a structure reaches the order of an overall deformation). The increase in residual may indicate the presence of coherent motions that are not accounted for by the set of OPs initially chosen. If the emerging modes couple to the previously defined set of OPs, long-time OP velocity auto-correlation tails are also expected. The remedy for this difficulty is to increase the number of OPs considered, a process greatly facilitated by the automated generation of OPs. Increase in the residuals may indicate the presence of an improbable fluctuation in the MD generated part of the finite ensemble used for a practical computation. This increase is generally minimized via the low $\underline{k}-\Phi_{k_{res}}$ sampling and, for the thermal-average forces, via the Boltzmann factor (structures with larger values of $\Phi_{k_{res}}$ for higher order $\underline{k}$ tend to be high in energy). However, for these cases, a simple reference structure renewal would suffice to account for the resulting motions, and additional OPs are not required.

As discussed above, new OPs should be added in order to redefine the constant OP ensemble (i.e., to eliminate the long-time tails of the correlation functions), and to account for the systematic growth of residuals that is not accounted for via re-referencing. In principle, a simple addition of higher order OPs to the set of existing ones, till the complete elimination of the long-time correlation tail would suffice. However, this might include some unnecessarily high frequency modes as OPs. As a result, the Langevin timestep should be reduced, affecting the efficiency of multiscale simulation. Efficiency can be restored by optimal choice of the OPs to be added. For example, one could carry out a ns conventional MD run and use the resulting configuration time courses to rank the omitted OPs according to their average rate of change. Variables that qualify as OPs are slow and coherent, whereas residuals (that are described by $\Phi_{k_{res}}$) are highly fluctuating with mean close to zero (further discussed below). The former are added, one at a time, to the list of existing OPs and new ensembles are generated by sampling the remaining variables. This is repeated till the residuals become reasonably small and the long-time tail in the auto-correlation function is eliminated. This procedure allows for addition of only slow variables and, hence, consideration of high frequency modes as OPs is avoided. Such a procedure may also be used in selecting OPs to start the software simulations.

Multiscale analysis provides a numerical simulation approach implied by the feedback between nano and atomic scale variables. As $\bar{\mathcal{F}}_k$ and $\overline{D}_{kk'}$ are OP-dependent, they should be computed at each Langevin timestep to account for the inter-scale feedback. A finite Langevin timestep $\Delta t$ advancement takes the OPs from time t to a time t+$\Delta t$ via Eq. (16). Thermal forces $\bar{\mathcal{F}}_k$ may be efficiently computed via an ensemble/Monte Carlo integration method enabled by the nature of the OPs. Atomic forces obtained from the residual generated OP constrained ensemble are used to calculate the OP force $\mathcal{F}_k^m$. Monte Carlo integration averaging of $\mathcal{F}_k^m$ over the ensemble is carried out to obtain the thermal $(\hat{\rho})$ average force $\bar{\mathcal{F}}_k$. Hence, the free-energy driving force is obtained via the all-atom probability density $\rho(\Gamma_0, \Phi)$, capturing the cross-talk between the OPs and individual atomic degrees of freedom. Since $\hat{\rho}(\Gamma_0, \Phi)$ reflects the OP constrained ensemble, the 6N atomic degrees are consistent with the state of the OPs. It should be noted that the definition of $\bar{\mathcal{F}}_k$ as OP derivative of free-energy in Eq. (14), and $\overline{D}_{kk'}$ as time integral of OP velocity auto-correlation function in Eq. (13) is independent of the linearity in the r–$\Phi$ relationship. This implies that the multiscale analysis developed can be applied to any complete set of slow variables provided the $O(\varepsilon)$ time scaling, and Newton's laws of motion hold for their dynamics. The presently disclosed OPs form a set of slow variables that has suitable properties to serve as a basis of the approach of the illustrative embodiment. It will be appreciated that other sets of slow variables can also be used in other embodiments, as long as the criteria of OPs dynamics are satisfied.

Adiabatic schemes have been successfully implemented to perform approximate quantum dynamics simulations and Car-Parrinello type ab initio quantum dynamics. The latter belongs to a family of extended Lagrangian approaches wherein the timescales of faster and slower degrees of freedom are adjusted to ensure the adiabatic propagation of the former in response to motions in the latter. This adjustment is achieved via attributing fictitious masses and kinetic energy to the faster modes. For many atom systems a free-energy profiling scheme, Adiabatic Free-energy Dynamics (AFED), based on an adiabatic partitioning of the slow and fast variables have been developed. AFED allows for application of higher temperature for the slow variables facilitating rare events sampling and high mass leading to an adiabatic decoupling. Therefore, the separation of timescale between those of OPs versus atomic dynamics, the relatively high OP masses $\bar{\mu}_k$, and the role of average forces for driving the slow variables across the free-energy landscape suggests implementation of an adiabatic dynamics algorithm for thermal-average force calculations. Unlike explicit variable transformation in AFED, extended phase space approaches like Temperature Accelerated Molecular Dynamics (TAMD) are also used for simultaneous propagation of slow and fast degrees of freedom. Solving the resulting equations of motion in the extended phase space is equivalent to solving Eq. (16) above. This bypasses explicit averaging. Another related approach, driven Adiabatic Free-energy Dynamics (d-AFED), employs explicit masses and dynamics closer to that of AFED in formulating TAMD. This allows direct generation of multidimensional free-energy surfaces for complex systems from the probability distribution function of the extended phase-space variables. Even though an adiabatic decoupling appears naturally in our analysis by the $O(\varepsilon)$ scaling of the Liouville operator, the relative efficiency of an adiabatic relaxation scheme versus the presently disclosed residual-generated sampling scheme remains to be determined. In particular, the presently disclosed scheme requires the development of a rich ensemble of atomistic configurations at each Langevin timestep, while the adiabatic scheme requires co-evolution of the slow and many $(O(N))$ fast variables. This issue is important for the efficiency of the simulation of systems involving $10^5$ or more atoms. However, in analogy to AFED, using higher temperature for propagating the slower variables (OPs here) would yield an algorithm for the simulation of rare-events phenomenon. This is further discussed below.

The diffusion factors may be computed via the correlation functions of Eq. (13) using short MD runs, because the correlation times in these functions are much shorter than the characteristic timescale of OP evolution. All factors in the OP dynamics equation, Eq. (16), are computed from the inter-atomic force-field via Monte Carlo integration and MD. Thus, the only element of the calibration in constructing the thermal-average forces and diffusions is through the existing force-fields (e.g., CHARMM or AMBER). At each Langevin timestep, the updated OPs are used to generate the atomistic configurations of the macromolecule; then, the host medium is introduced via a re-solvation module and the entire system is thermalized. An ensemble of such equilibrated atomistic configurations is used to generate the thermal-average forces and diffusions. The latter factors are used to update the OPs completing one cycle of the Langevin timesteping.

According to the present disclosure, the OPs are defined over the macromolecule. As with the atomic configurations of the macromolecule, water and ion are accounted for via the quasi-equilibrium ensemble (i.e., the configuration of the water and ions rapidly explores a quasi-equilibrium ensemble at each stage of the OP dynamics). This assumption holds only when water/ion equilibrate on a timescale much smaller than that of OPs. Similar re-solvation scheme has been used with OPs in simulating virus capsid expansion in $Na^+$ and $Ca^{2+}$ solutions. Fluctuations from water and ions modulate the residuals generated within the MD part of the constant OP sampling and affect the thermal-average force. As such, the water and ions in the definition of the Ops (as discussed above). If slow hydrodynamic modes are found to be of interest, these atoms may be included in the definition of the OPs. Ions tightly bound to the macromolecule are considered a part of OPs. After every Langevin timestep, an ion accessible surface is constructed, and ions close to the surface are tracked during the MD ensemble enrichment calculation. Ions with appreciable residence time within the surface are included in the definition of the OPs henceforth.

The notion of water and ion dynamics being much faster than a set of slow modes is similar to that used in Normal Mode Langevin (NML). If these fast modes correspond to the coordinated motion of just a few atoms, then there is no clear separation in their timescale from that of single atom vibrations. Such fast modes cannot be described by Langevin dynamics unless memory kernels are used. However, NML identifies the modes by diagonalizing a Hessian matrix and fully relaxes (over-damps) the high frequency modes near their energy minimum (respecting the subspace of low frequency normal modes). In the limit of a large damping coefficient, this is equivalent to using Brownian dynamics to propagate high frequency modes. By contrast, in the presently disclosed approach, rapidly fluctuating variables are allowed to explore a representative ensemble of configurations. Using the over-damped value of the fast variables to construct an all-atom configuration and using that configuration to compute the OP force neglects the difference between the OP forces as a function of the average configuration versus the average of the OP force over an ensemble of atomic configurations. Hence, over-damping of fast modes is avoided. Furthermore, the NML approach would become computationally expensive for the N of O ($10^6$) atom systems of interest. The presently disclosed approach avoids the need to diagonalize a large Hessian matrix, a feature that follows directly from the explicit formulation of the order parameters via Eq. (2) and Eq. (4). Finally, the OPs are essentially normal modes in that they are linear combinations of atomic positions and furthermore are slowly varying. The equations of motion are highly nonlinear in the OPs and are dissipative. Thus, unlike a normal mode analysis, the presently disclosed formulation can account for states that are far from a free-energy minimizing structure.

As mentioned above, for some choice of initial data, the $O(\varepsilon)$ contribution to $\tilde{W}(\underline{\Phi}, t)$ can have short timescale dependence (e.g., due to a shock wave). Under this condition, the basic assumption of the lowest order quasi-equilibrium behavior is violated, as the $O(\varepsilon)$ scaling of the OP motion is disturbed. In such a case, one expects Fokker-Planck behavior. The present formulation may be generalized to accommodate such inertial effects. For the macromolecular phenomena considered below, however, this class of initial data is ignored.

A study was undertaken to assess the viability of the OPs described above as a basis of a multiscale algorithm for simulating macromolecules. An evaluation of other variables in this context was also obtained. Comparisons with traditional MD were made to determine the accuracy and efficiency of the method. All multiscale simulations were done using software based on the OPs and the multiscale analysis described above. The CHARMM22/27 force-field and NAMD were incorporated into the software as part of the computation of the thermal-average forces and diffusion factors for the OPs.

The demonstration system was the RNA of a Satellite Tobacco Mosaic Virus (STMV). This molecule contains 949 nucleotides. The initial state of the system was believed to be at equilibrium when the RNA resided with the associated proteins within the STMV capsid. Evolution followed instantaneously after the capsid was removed. The host medium was 0.3M NaCl solution and the temperature was 300K. The system was placed within a cube and NVT conditions were applied. Details of the NAMD settings are given in Table 1 below. Software simulations were done in these conditions, and not those used in other studies, as more dramatic structural changes occur because the RNA is more stabilized by $Mg^{2+}$ than by $Na^+$. This is because $Na^+$ is expected to be diffusively bound to RNA, whereas $Mg^{2+}$ remain tightly bound.

TABLE 1

| PARAMETER | VALUE(S) |
| --- | --- |
| Temperature | 300 K |
| Langevin damping | 5 |
| Timestep | 1 fs |
| fullElectFrequency | 2 fs |
| nonbondedFreq | 1 fs |
| Box size | 145Å × 145Å × 145Å* or 162Å × 162Å × 162Å** |
| Force-field parameter | par_all27_prot_na.prm |
| 1-4scaling | 1.0 |
| Switchdist | 10.0 Å |
| Cutoff | 12.0 Å |
| Pairlistdist | 20.0 Å |
| Stepspercycle | 2 |
| Rigid bond | Water |

*Box for free RNA simulation for 3 ns.
**Box for free RNA simulation from 3 ns-50 ns and protein-bound RNA.

As mentioned above, the slowness in rate of change of a typical OP (001Z) was examined to ensure its applicability within the multiscale framework. The OP considered, in particular, exhibited properties of dilation/extension about the Z-axis. The time evolution of this OP was compared to other variables to validate that some of the latter are not suitable as slow variables for the purpose of a multiscale analysis. If the fluctuations in these variables probe short space-time events, then they are expected to be accounted for by the quasi-equilibrium ensemble; otherwise, larger space-time events are accounted for by one or more of the OPs.

Some other variables commonly used to characterize macromolecules, denoted "structural parameters" (SPs) herein, may be compared with the dynamics of the OPs described above. The SPs analyzed in the present disclosure are different types of dihedrals and their cosines, radius of gyration, end-to-end distances, and typical components of the unit vectors along the bonds connecting monomers. These SPs are designated herein as $SP_1$, $SP_2$, $SP_3$, and $SP_4$, respectively. Each of these SPs was calculated over a 1 ns MD trajectory for the RNA under conditions mentioned above. The moving averages were calculated over a window of 50 ps to filter out the coherent part of the variations from the fluctuations ($\lambda$). Details on $\lambda$ computation are provided below in Appendix D. The time evolution of the dihedrals $\gamma, \delta$ and $\varepsilon$ depends on their location in the back bone. $\delta$ fluctuates the least due to geometric constraints imposed by a five membered ring. In contrast, those not associated with the backbone fluctuate even more than $\gamma$ or $\varepsilon$. Fluctuations of variables characterizing the overall size of the macromolecule, like $SP_2$ or $SP_3$, are much smaller. For $SP_4$, fluctuations are maximum, and are also sensitive to bond location.

The time evolution of these SPs was compared to that of the OPs described above. Fluctuations in $SP_1$ and $SP_4$ were several orders of magnitude higher in amplitude than those for the OPs, and/or their characteristic timescale was much shorter. Hence, they do not evolve slowly and cannot serve as a basis of a multiscale analysis. Finally, $SP_2$ and $SP_3$ are suitable as OPs but do not readily enable the generation of SP ensembles, as they are a subset of a more general set of OPs. This presents difficulties in computing thermal-average forces and diffusion factors needed for a multiscale analysis. In contrast, the OPs described above are automatically generated, and therefore the set $\Phi$ can be augmented for systems of higher complexity. Furthermore, the end-to-end distance and radius of gyration are accounted for via the more general OPs (shown below).

As system size increases, the OPs become better filters of the high frequency fluctuations. To validate this, heptaalanine with 8000 water molecules was simulated in a cubic box of side 44 Å under settings set forth in Table I. Fluctuations in OPs for larger systems are found to be much smaller than those of smaller ones (i.e., the same OP shows amplified fluctuations as the system is changed from RNA to heptaalanine). Distinct differences in length scales allow better separation of the lower order OPs from those of the higher ones in the RNA. This facilitates filtering of the low and high frequency modes. For smaller systems like heptaalanine, the length scale separation diminishes. Thus, OPs cannot facilitate filtering of high frequency fluctuations, and consequently the implementation of multiscale analysis becomes inefficient.

Figure 6A:
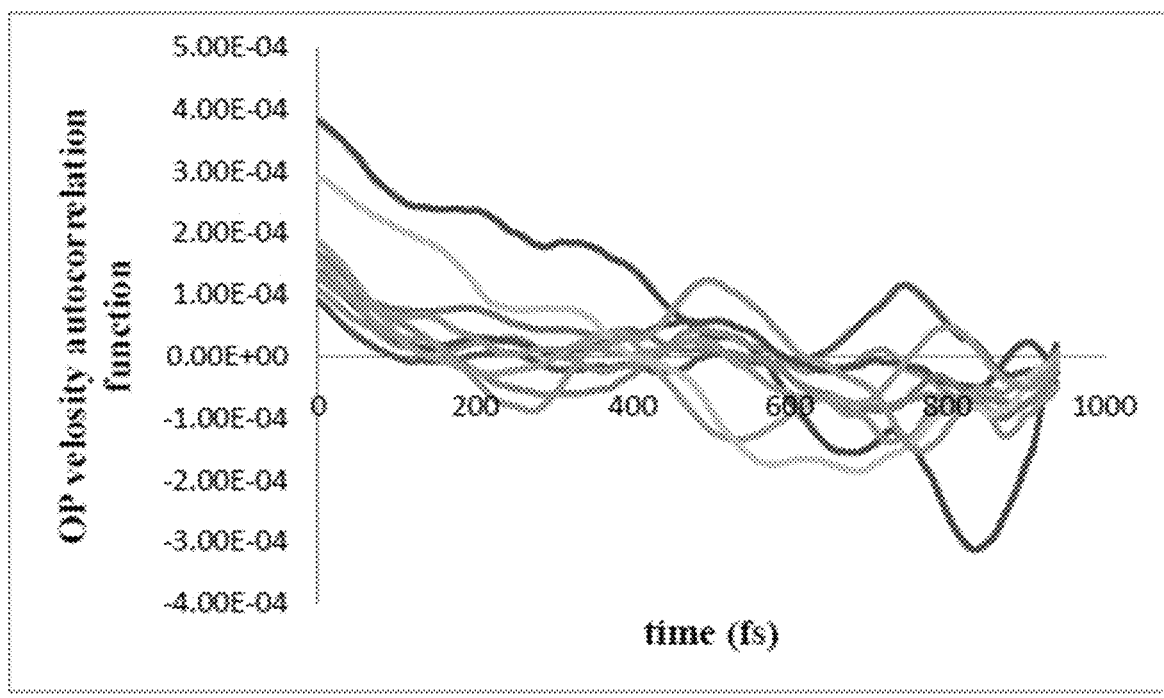
FIG. 6A is a diagram showing ten order parameter (OP) velocity auto-correlation function time-courses for 001Z starting from same initial conditions but different initial velocity random seeds.
Figure 6B:
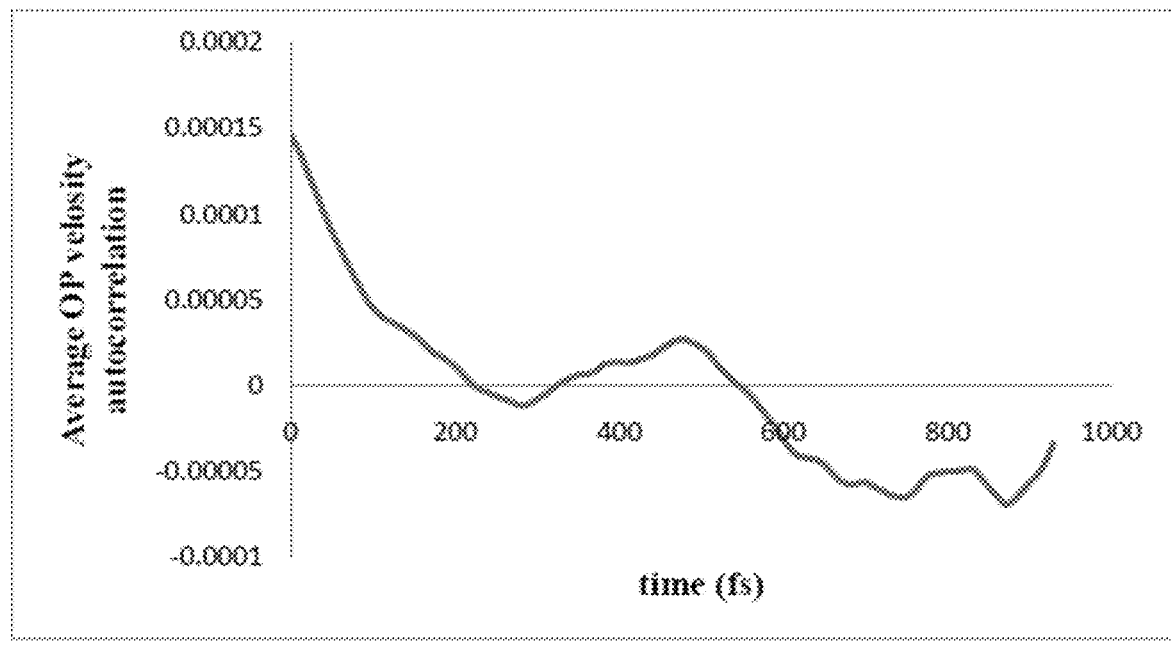
FIG. 6B is a diagram showing a Boltzmann average OP velocity auto-correlation function time-course showing the absence of a long-time tail and the lack of coupling to other slow variables not included in the set of OPs.

The choice of OPs depends on the characteristics of the system of interest. This can be understood a priori via analyzing OP evolution for short MD trajectories and observing the decay in the OP velocity auto-correlation functions. It was found most efficient for the present problem to only use 4 OPs (i.e., the center of mass and 3 corresponding to overall extension-dilatation). To verify completeness of this set of OPs for the present problem, the OP velocity auto correlation functions were plotted for a window of 1 ps. The correlation decayed sharply on a timescale much shorter than that of OP evolution (i.e., the OPs were constant over the time of auto-correlation decay). The decay zone was followed by a fluctuating phase that reflects insufficient statistics for constructing long-time correlation function behavior. FIG. 6A illustrates a plot of several auto-correlation functions for 1 ps trajectories with identical starting structure and initial conditions but different random seeds for generating initial velocities. In principle, an average of such single MD simulation derived correlation functions is required to compute the diffusion factors. However, using only the early part of a single MD correlation function (wherein the most statics are accumulated), as shown in FIG. 6B, was found to suffice. Furthermore, the correlation analysis validates the completeness of the set of Ops, as there is no long-time tail behavior in the correlation functions.

Omission of a slow variable that couples with the existing set can lead to a long-time correlation tail. To validate this, the correlation calculation was redone without the 100X OP. This led to a long-time tail in the velocity auto-correlation function for the 001Z and 010Y OPs. In general terms, the deformational behavior in a given Cartesian direction is driven by forces that depend on the OPs in all directions. Therefore, a missing OP will create an ensemble of atomic configurations that reflect its absence, which in turn is expressed in slower behavior of the retained OP velocities, and hence the associated auto-correlation functions. Simultaneously, the ensemble had a major population of structures with very high residuals (~10 Å), also signaling omission of a slow mode. Therefore, the diffusion calculation indicates the absence of a key slow variable that can be optimally added to the existing set via the procedure described above. Due to orthogonality of the basis functions described above, the cross-correlation functions between different OPs are several orders of magnitude smaller than the auto-correlation functions; this implies that the OPs are not coupled through the diffusion factors but only through the OP dependence of the thermal-average forces. This greatly simplifies the construction of the random forces as they are related to the diffusion matrix.

Constructing higher order OPs from an MD run via Eq. (4) shows that they are highly fluctuating and therefore not appropriate as OPs. Rather they are accounted for via the quasi-equilibrium probability density (i.e., in the ensemble used to calculate averages). As discussed above, the ensemble of atomistic configurations is generated via Eq. (2). The residuals ($\bar{\sigma}_i$) are generated by a formula similar in structure to that used to obtain the atomic positions, but the sum over basis functions do not include those associated with the OPs.

Addition of OPs to a pre-existing set is needed in various cases. If the system is changed (e.g., if it is composed of multiple macromolecules), then more OPs are required to form a complete set. The added OPs probe complex inter-macromolecular motions. New OPs could also be added in a dynamic fashion in the course of a simulation to account for types of motions absent initially. As mentioned above, the appearance of long-time tails in the correlation functions later in a simulation is a key indicator of the need to augment the set of Ops.

Figure 7A:
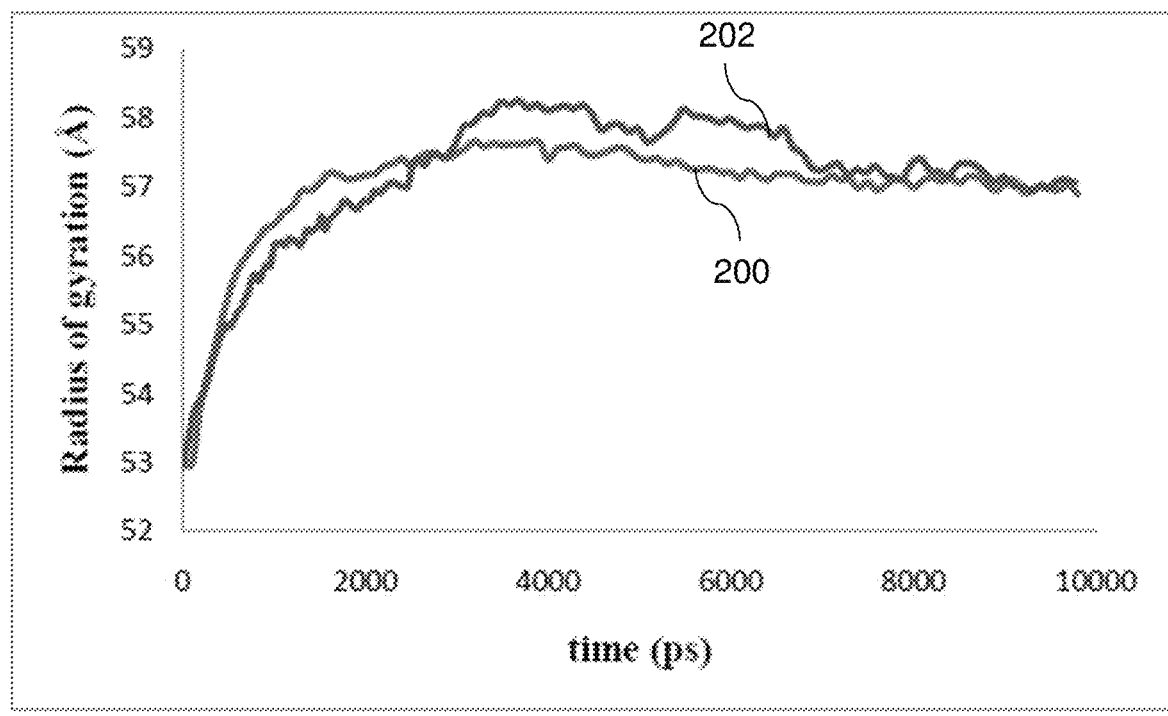
FIG. 7A is a diagram showing time evolution of the radius of gyration, generated using conventional MD and the presently disclosed software.
Figure 7B:
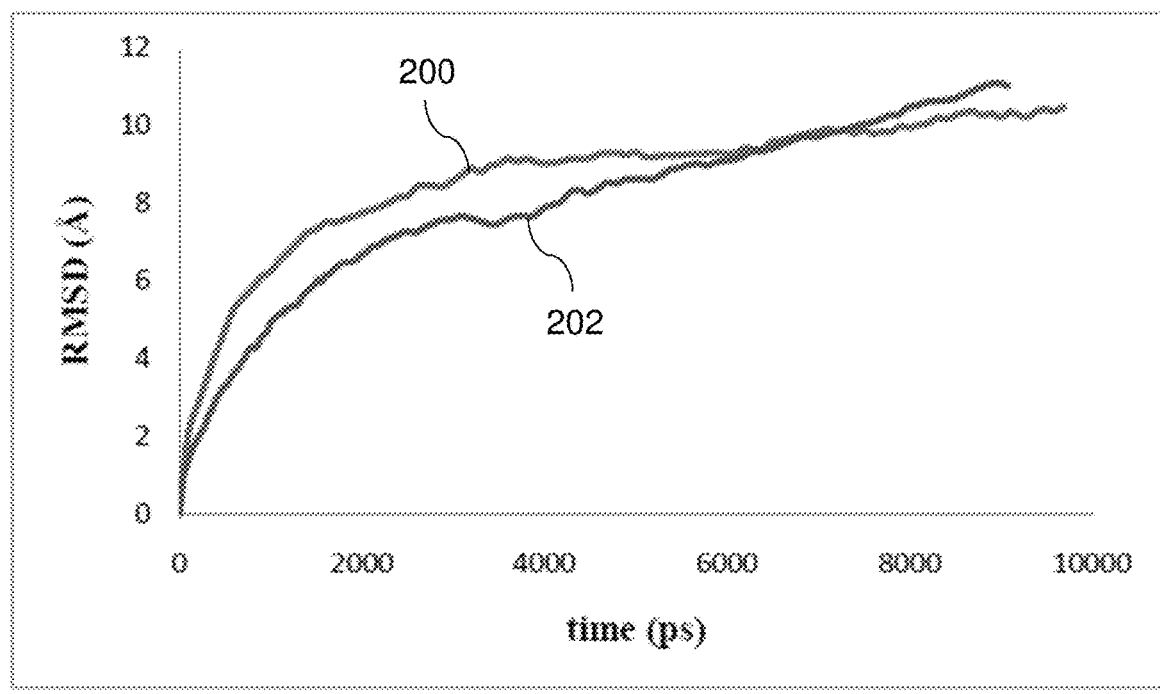
FIG. 7B is a diagram showing RMSD from the 0 ns structure to that after 10 ns, generated using conventional MD and the presently disclosed software.
Figure 7C:
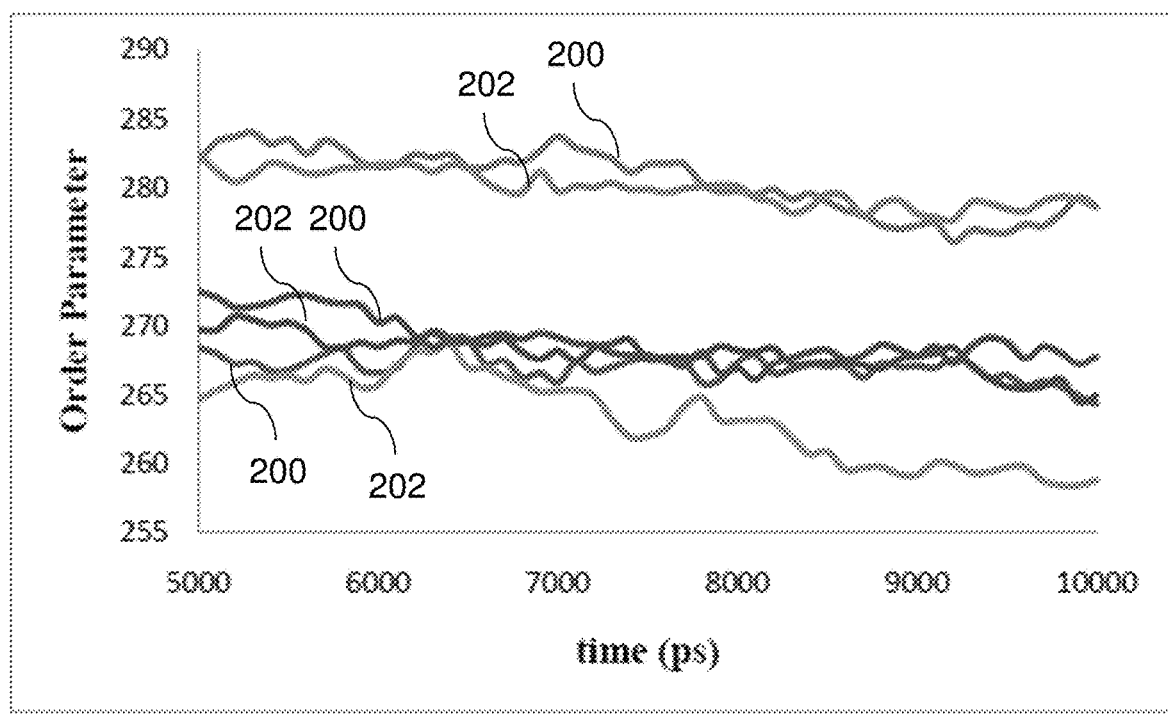
FIG. 7C is a diagram showing the values of OPs 010Y, 100X, and 001Z, generated using conventional MD and the presently disclosed software.
Figure 7D:
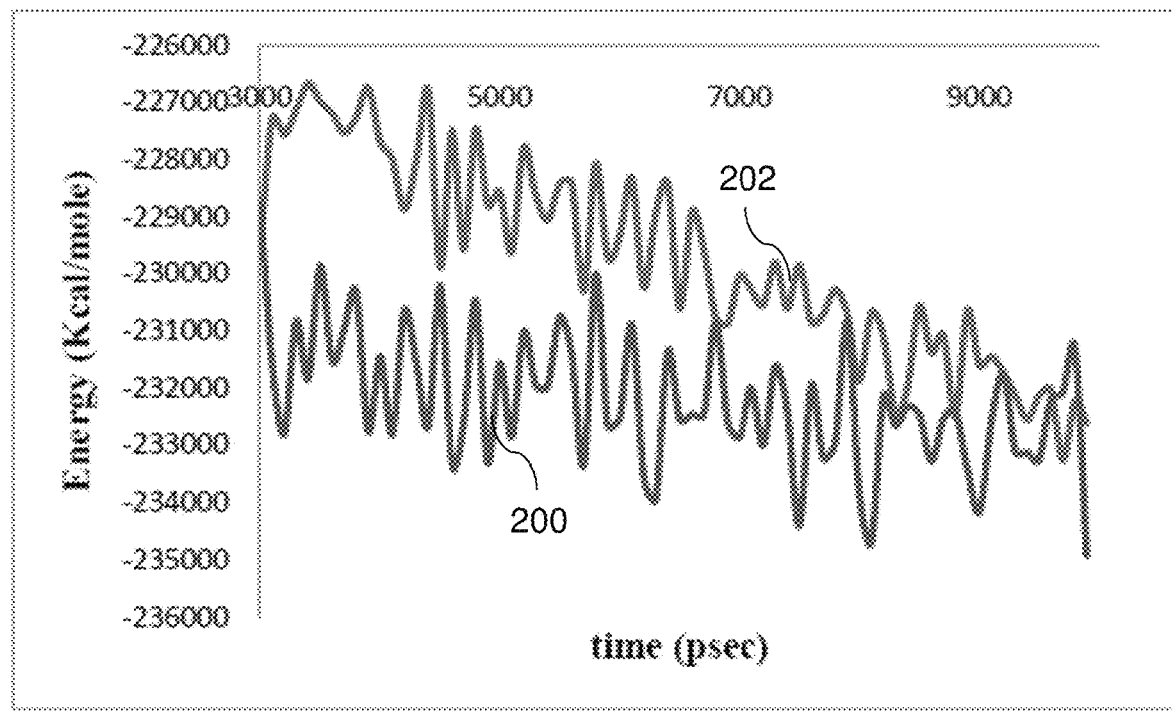
FIG. 7D is a diagram showing RNA potential energy, generated using conventional MD and the presently disclosed software.
Figure 7E:
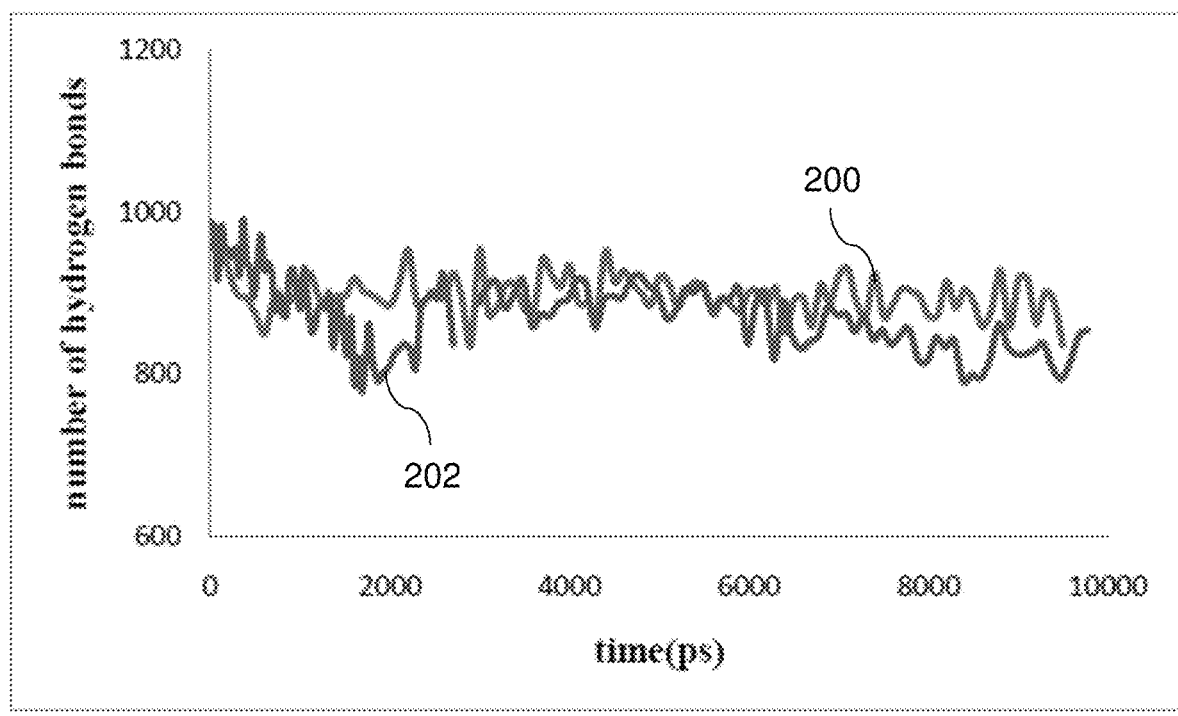
FIG. 7E is a diagram showing the number of nucleic acid-nucleic acid hydrogen bonds, generated using conventional MD and the presently disclosed software.

To assess the accuracy of the multiscale OP dynamics, comparisons were carried out with conventional MD simulations for trajectories of 10 ns. On removal of the viral capsid, the RNA is no longer constrained and tends to expand. Following initial expansion, the RNA shrinks and finally fluctuates among a range of distinct atomistic states of similar energy. FIG. 7A shows the radius of gyration obtained with MD 200 and with the presently disclosed software 202, while FIG. 7B shows the progress of the RMSD from the initial structure as a function of time. Agreement of the radius and the RMSD between MD and the multiscale simulation is excellent. FIG. 7C plots OP time courses from the final 5 ns of conventional MD 202 and the presently disclosed software 202. These results show that both the structures are essentially a part of similar OP ensembles having similar overall characteristics, and confirm that the multiscale simulation is generating configurations consistent with the same value of the OPs that arise in MD. However, the presently disclosed software actually corresponds to an ensemble of MD simulations (see below). Significantly, the multiscale simulations capture the overall structural dynamics, which is often the main interest. However, the atomistic configurations are also accounted for via the quasi-equilibrium distribution. This illustrates that radius of gyration and end-to-end distance (as mentioned above) is accounted for by our OPs. FIG. 7D shows the potential energy for the multiscale simulations, which fluctuates about a constant value. Energies show identical trend and are within a percent of those from the MD run. This shows that the RNA gains stability as the potential energy gradually decreases. Energies from the MD and software generated trajectories 200, 202 show excellent agreement in trend as well as in magnitudes. The observed difference is within limits of those from multiple runs starting from the same initial structure with different initial velocities. As another basis of comparison, time evolutions of the number of intra-macromolecular hydrogen bonds for both methods are shown in FIG. 7E. Hydrogen bonds are defined solely on the basis of geometric parameters (bond angle: 20°; bond-length:3.8 Å) between donors and acceptors. Initial expansion reduced the number of these bonds (primarily the ones involved in the RNA tertiary structure). The number of bonds decreased less rapidly in the later part of the trajectories when expansion ceased. A detailed account of the various types of hydrogen bonds is given below.

One advantage of multiscaling is the potential to use timesteps of tens or hundreds of ps or greater (in contrast to the $10^{-15}$ sec of conventional MD or 0.2-1 psec for the Langevin PCA approach). For relatively slow processes in large systems, the speed-up over conventional MD is significant. 128 processors were used to assess the efficiency of the presently disclosed multiscaling approach. During the initial transient, 40 ps timesteps were used. To accommodate the initial expansion and account for the structural anisotropy, the RNA was re-solvated in a bigger box (Table 1) after the first 3 ns. Post-initial transient, Langevin evolution was executed using 150 ps timesteps, reflecting the longer characteristic time for this phase. In this slower evolution regime (probed till 50 ns for the study), efficiency becomes 11 fold. However, comparison with a single MD run is not appropriate since the software corresponds to ensemble MD. In this study, a single software simulation corresponds to an ensemble of 168 traditional MD runs. While, for each MD run, the OP time-course is essentially the same as that predicted by the software, the detailed atomistic configuration varies dramatically among members of the ensemble. This factor of 168 comes from the sample size used in the Monte Carlo integration to compute the thermal-average forces. Finally, a single MD run may not be representative of an ensemble of possible time courses, which, in contrast, is automatically overcome in the presently disclosed approach. If the finer short timescale structural transition is of interest, it can be pursued by either shorter timescale traditional MD runs or by including more OPs (although this will decrease the minimum characteristic time of OP dynamics and, therefore, reduce the efficiency of multiscale simulations). Unlike the Langevin PCA model, where single or multiple ns MDs are used to generate input, here only short ps MDs are required to generate a constant OP ensemble and an equivalent trajectory ensemble. Selecting OPs for running the multiscale simulation requires an initial analysis of their time trends over 1 ps-1 ns timescale. However, this analysis need not be repeated in the course of simulations until the emergence of new OPs, thereby restoring efficiency of the multiscale simulation.

Figure 8:
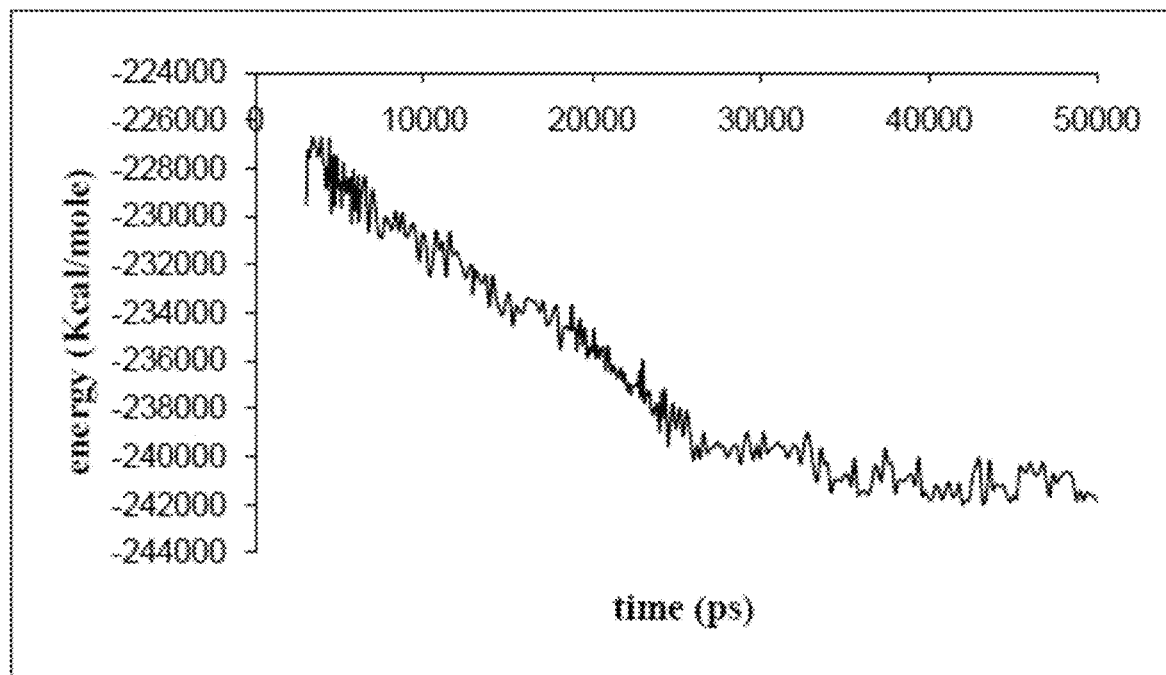
FIG. 8 is a diagram showing time evolution of the RNA potential energy via a 50 ns simulation using the presently disclosed software.
Figure 9:
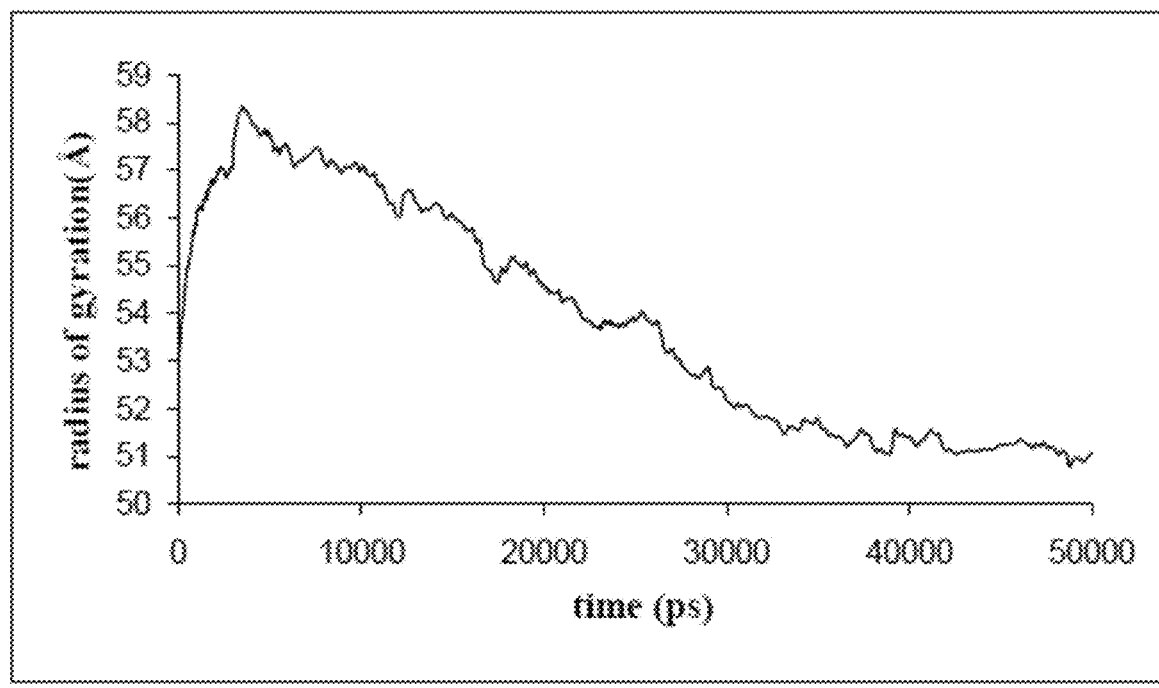
FIG. 9 is a diagram showing time evolution of the RNA radius of gyration via a 50 ns simulation using the presently disclosed software.
Figure 10A:
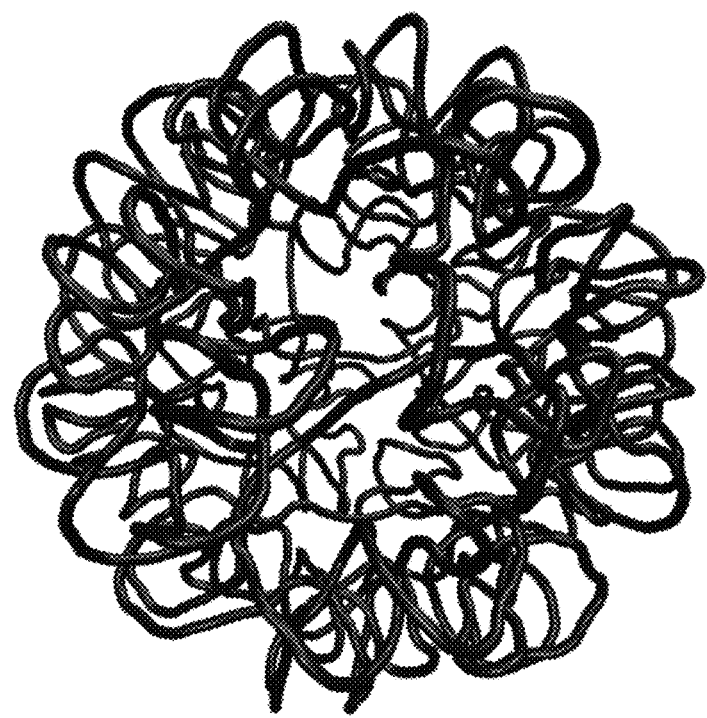
FIG. 10A is a diagram showing an RNA structure snapshots at 0 ns.
Figure 10B:
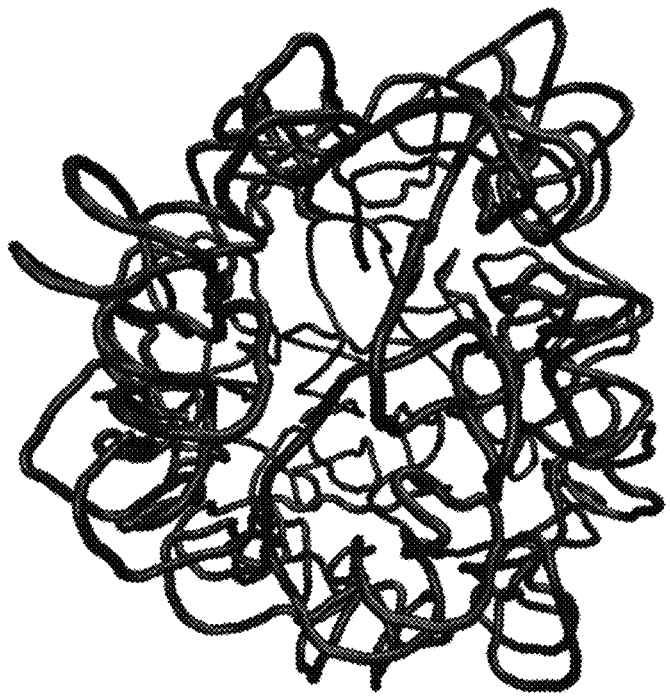
FIG. 10B is a diagram showing an RNA structure snapshots at 10 ns.
Figure 10C:
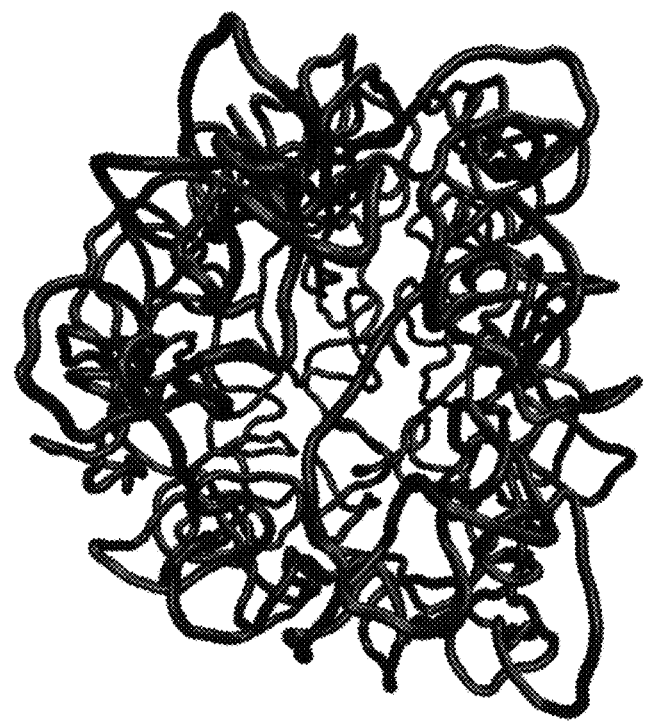
FIG. 10C is a diagram showing an RNA structure snapshots at 20 ns.
Figure 10D:
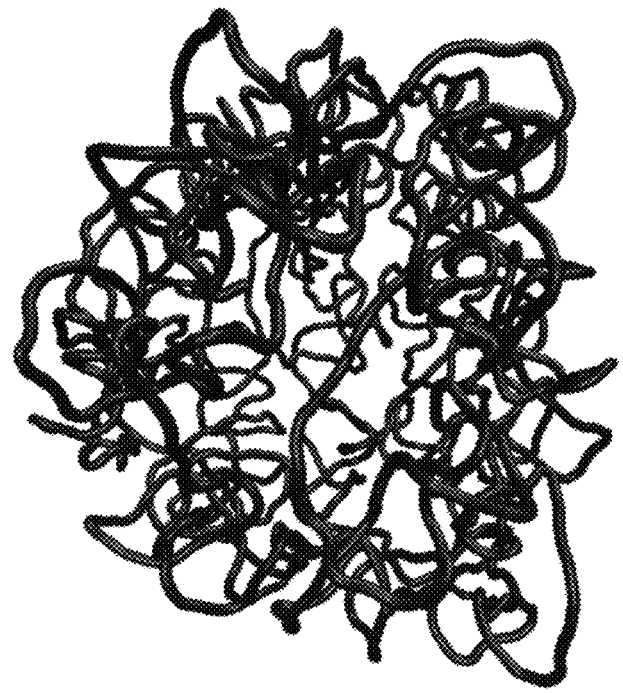
FIG. 10D is a diagram showing an RNA structure snapshots at 30 ns.
Figure 10E:
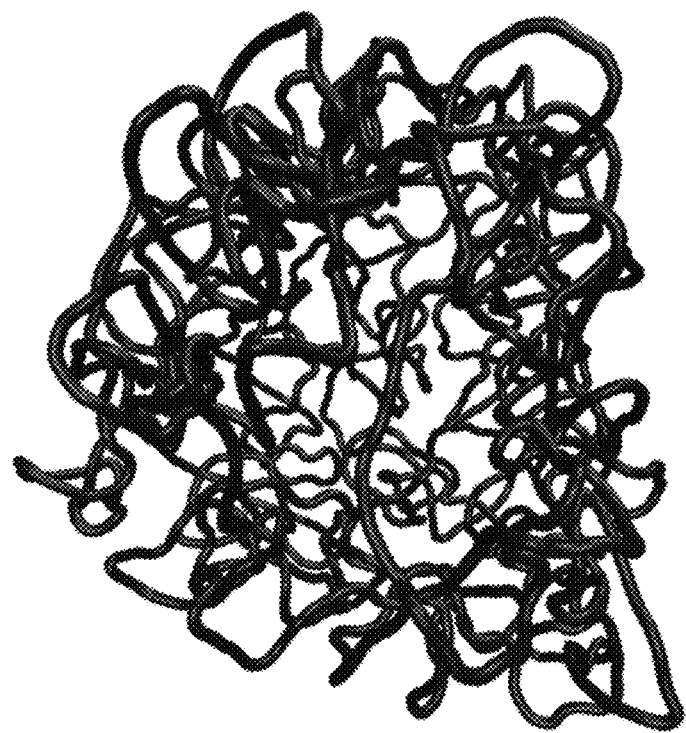
FIG. 10E is a diagram showing an RNA structure snapshots at 40 ns.
Figure 10F:
FIG. 10F is a diagram showing an RNA structure snapshots at 50 ns.
Figure 11:
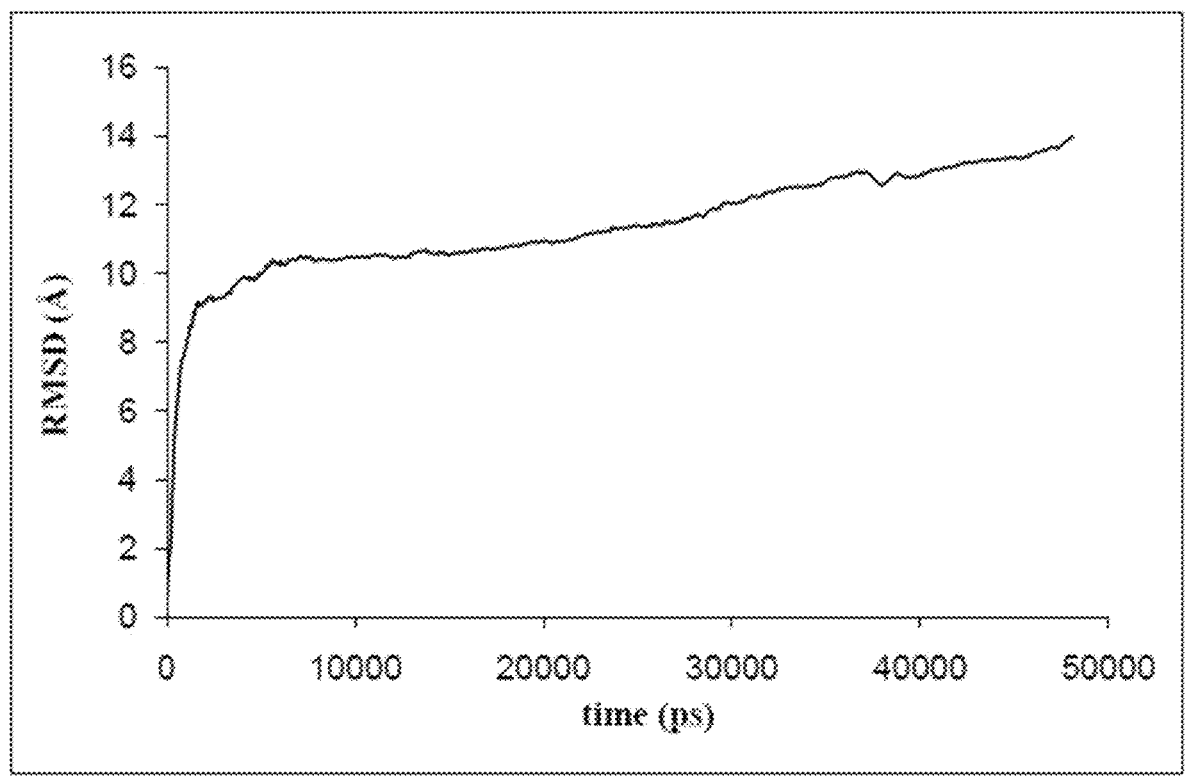
FIG. 11 is a diagram showing RMSD from the 0 ns structure to that after 50 ns, generated using the presently disclosed software.

Making use of the above efficiency, the long-time behavior of the RNA was probed using the presently disclosed software. FIG. 8 shows a plot of potential energy versus time for the RNA. The energy decreases and fluctuates about a minimum. FIG. 9 shows a plot of the radius of gyration for the 50 ns trajectory. Following rapid initial expansion, RNA gradually shrinks for 30 ns before reaching a dynamic equilibrium, wherein it fluctuates about 50 Å. These overall changes in shape and size are tracked by the OPs. Their values also gradually decrease before flattening out. However, the magnitude of the three OPs is different, probing different extents of deformation along the three Cartesian axes. This is consistent with the fact that even though overall shape and size follow simple trends (reflected in FIG. 9), the anisotropy in the system leads to a symmetry breaking which is tracked by the OPs and the constant OP ensemble. FIGS. 10A-F validate that the initial symmetry is completely lost in the course of the simulation. In the final structure, shown in FIG. 10F (after 50 ns), the tertiary structure of the RNA is highly disrupted, though secondary structure still remains. The latter is in agreement with experiments that suggest free RNA can possess some secondary structure. FIG. 11 shows the RMSD over the entire 50 ns trajectory. RMSD shows a rapid increase followed by a gradual one. The increase in RMSD over the final 20 ns trajectory signifies that even though the energy, overall shape and size (OPs) change negligibly, there are local (non-coherent) changes that are accounted for by the constant OP ensemble (i.e., fluctuations in the higher order OPs). Thus, the presently disclosed software captures the exploration of multiple iso-energetic configurations by the RNA.

Figure 12:
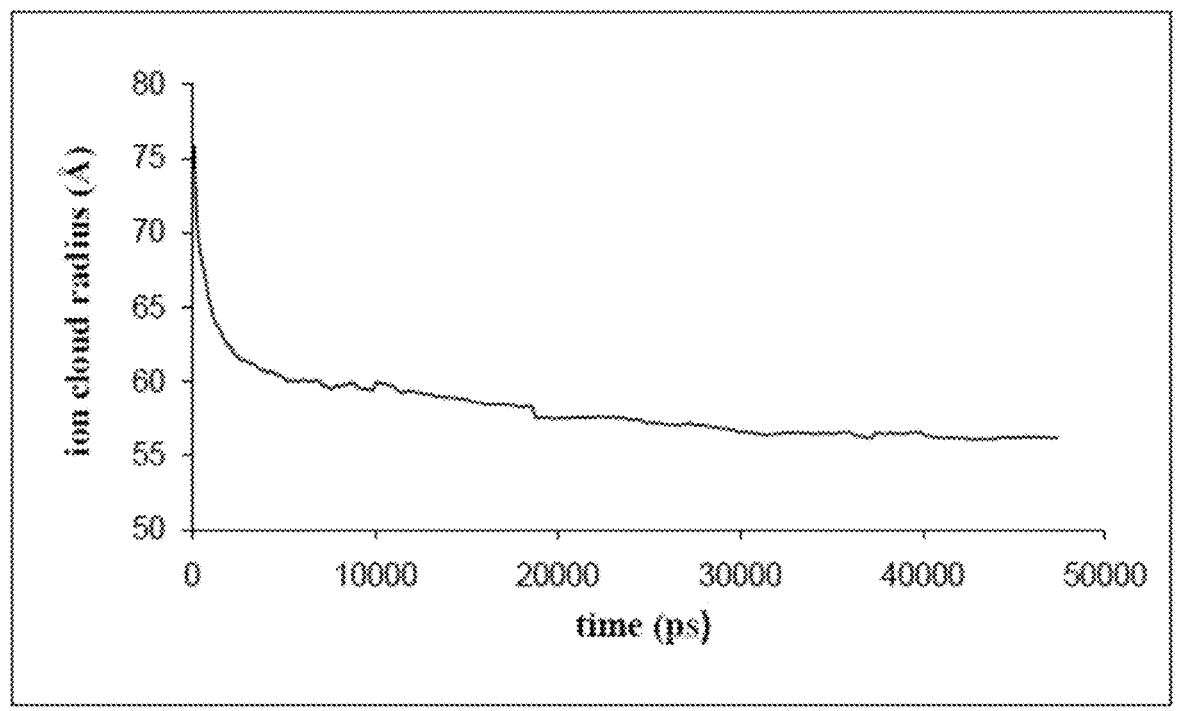
FIG. 12 is a diagram showing time evolution of a mobile ion (Na+) cloud radius over 50 ns.
Figure 13A:
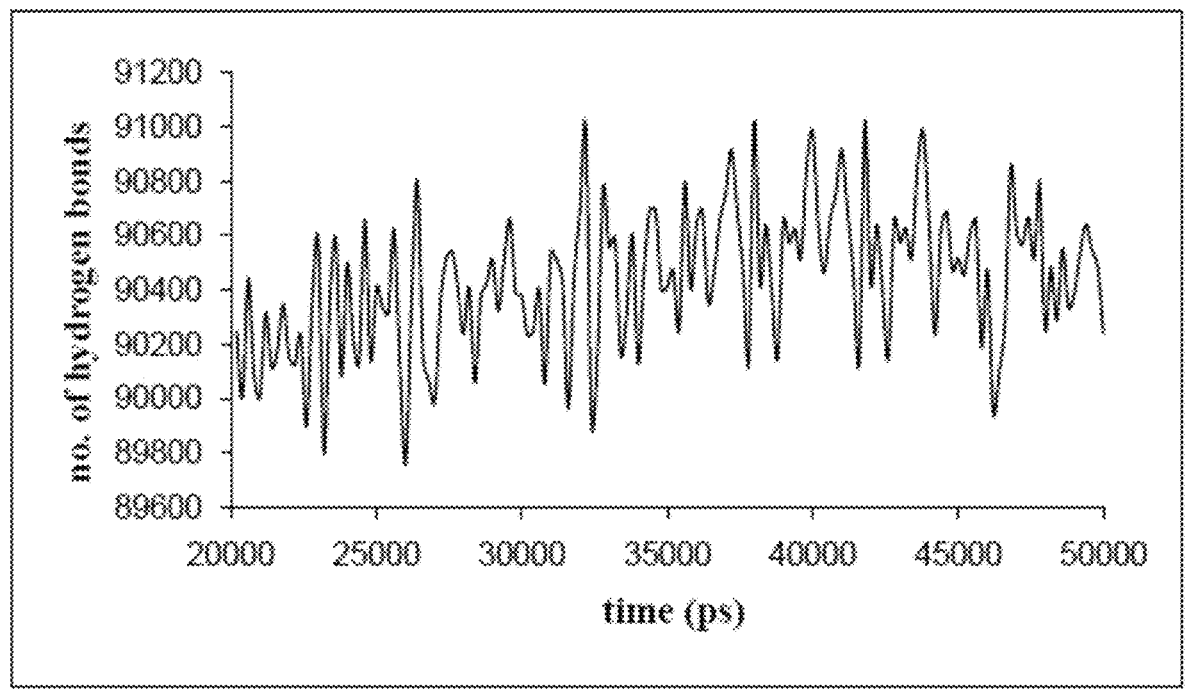
FIG. 13A is a diagram showing time evolution of the water-water hydrogen bonds for simulated RNA dynamics during the final 30 ns of the simulation of FIGS. 10A-F.
Figure 13B:
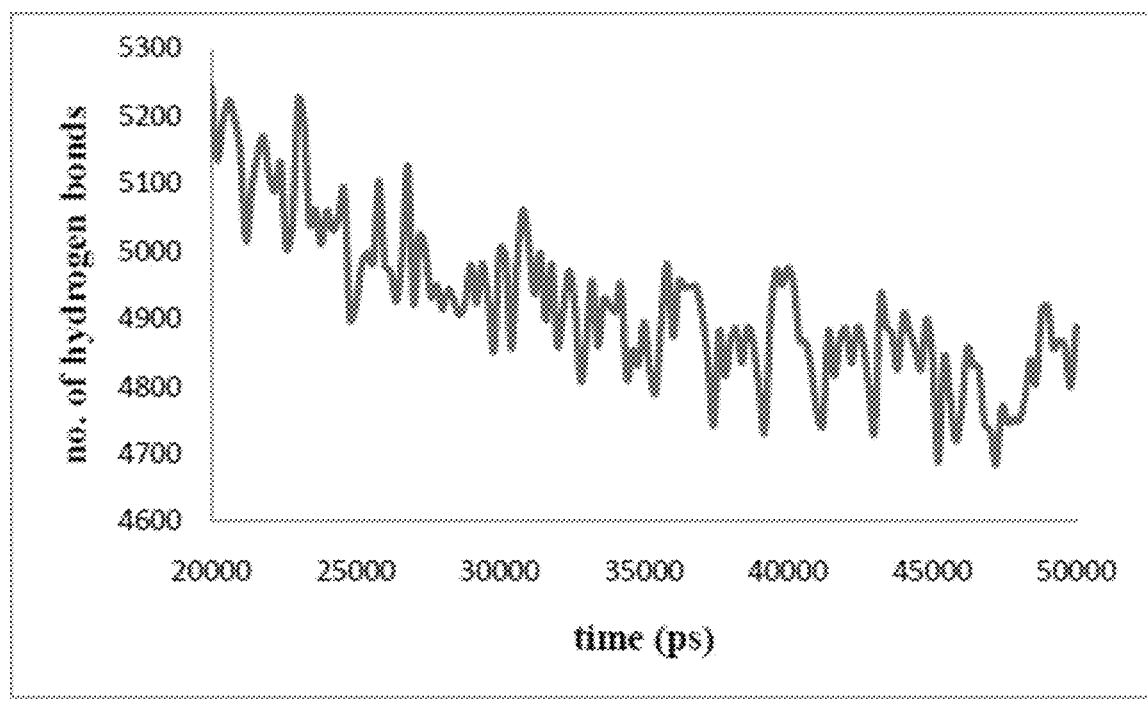
FIG. 13B is a diagram showing time evolution of the nucleic acid-water hydrogen bonds for simulated RNA dynamics during the final 30 ns of the simulation of FIGS. 10A-F.
Figure 14A:
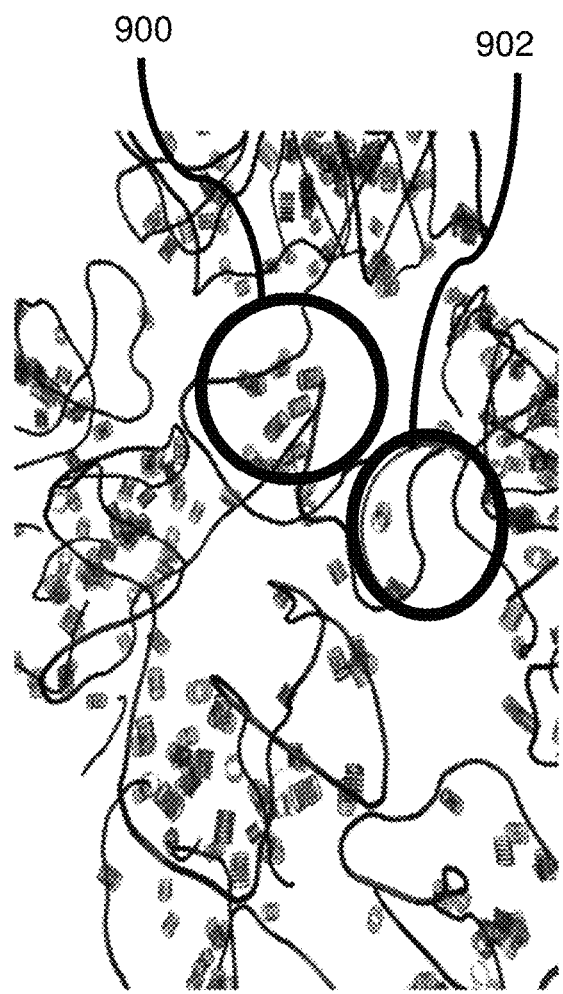
FIGS. 14A and 14B are depictions showing a shift in hydrogen bonds from a first region to a second region.
Figure 14B:
Figure 14C:
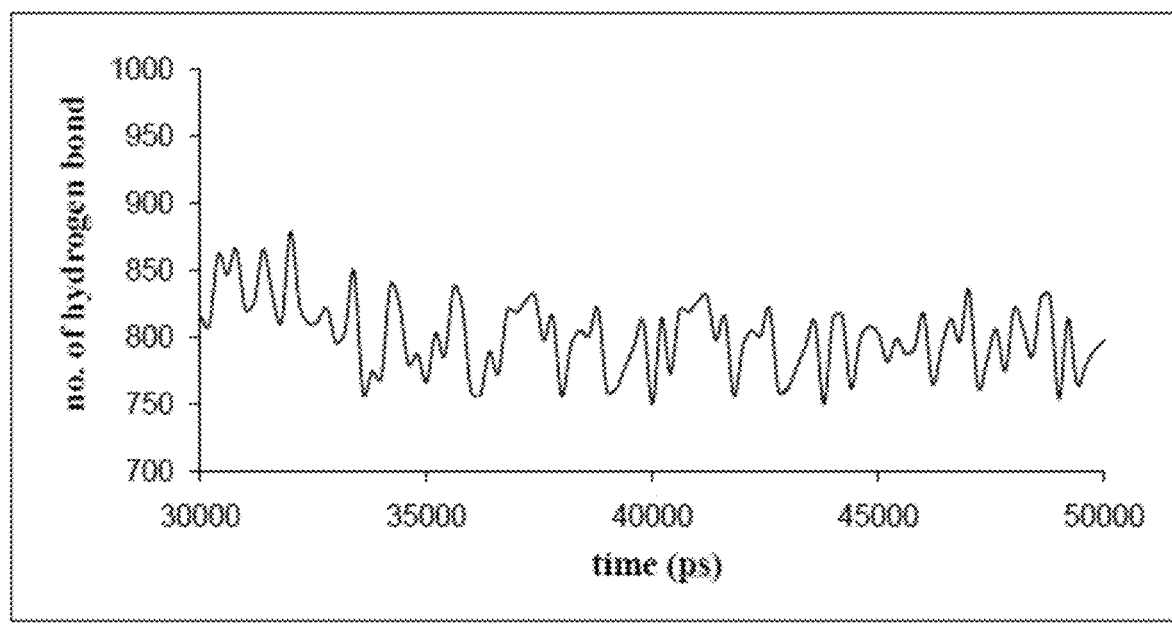
FIG. 14C is a diagram showing time evolution of the number of nucleic acid-nucleic acid hydrogen bonds for the final 20 ns of the simulation of FIGS. 10A-F.

The gradual shrinkage of RNA is explained on the basis of ion shielding effects. FIG. 12 shows that the radius of the ion cloud deceases with time. Thus, the ion cloud concentrates and distributes about the RNA, shielding the electrostatic repulsion between similarly charged nucleic acid residues in the RNA, causing them to come closer. When the cloud is removed, similarly charged groups mutually repel, and the RNA expands instead of shrinking. To confirm the above physical picture, the structure at the end of 20 ns was de-ionized and a further 7.5 ns simulation was carried out in aqueous solvent. The expansion due to electrostatic repulsion was reflected in the radius of gyration and OP changes over this simulation. A 1:1 electrolyte was used since the ions are diffusively bound and exchange positions (unlike for tightly bound ions such as $Mg^{2+}$), justifying their inclusion as a part of the ensemble and not as an OP. Even though the ions are not included in an OP calculation, their rapid quasi-equilibrium redistribution accompanying structural changes in the OP defined macromolecule at each Langevin timestep correctly accounts for the ion cloud around the RNA. Closely related to the distribution of ions is the distribution of water and hydrogen bonds. The total number of hydrogen bonds remains constant throughout the 50 ns simulation. However, the number of nucleic acid-water hydrogen bond decreases, while those for water-water hydrogen bonds increases, conserving the total number of bonds, as shown in FIGS. 13A and 13B. This phenomenon is consistent with mobile ion screening induced RNA shrinkage. As the RNA shrinks, water from the inner RNA cavity is expelled, thereby increasing the number of bulk water-water interactions. These shifts in sodium ion population, coordinated with hydrogen bond rearrangement, guide the system to the final structure. There is also a re-distribution of inter-nucleotide hydrogen bonds as the RNA samples iso-energetic configurations in the final 20 ns. This shift in hydrogen bonds is shown between FIGS. 14A and 14B (from region 900 to region 902). However, the total number of nucleic acid-nucleic acid hydrogen bonds is conserved, as shown in the plot of FIG. 14C.

While coherent structural dynamics are tracked by changes in the OPs, additional high frequency macromolecular motions are captured by the residual modified/MD generated ensemble. These high frequency modes capture small-timescale local alterations, over and above the OP mediated deformations in the RNA, and consequent effects on atom scale features like the hydrogen bond distribution. However, other complex and/or slow modes like bending or twisting can arise in the course of the RNA dynamics and affect the hydrogen bonds. As stressed above, emergence of new modes can be captured by the OPs described above and are signaled by the self consistency checks. Within the simulated period of time (50 ns), no long-time velocity auto-correlation tails or significant populations of high residual structures signifying the absence of additional slow modes were detected. A plausible explanation is that in viral RNAs it is possible that the bending modes leading to an unfolding transition appear much later in the time course (>50 ns) of structural evolution or secondary structure disruption occurs at a temperature much higher than 300K. Another possibility is the sampling limitation of the presently disclosed approach. RNA unfolding has typically been modeled using higher temperature sampling techniques, like replica exchange MD. Such sampling techniques can take into account contributions from rare events and prevent entrapment of a structure in deep potential wells. Most of the simulation results presently disclosed are independent of such events, however, as they deal with reaching the energy minima rather than being entrapped in one. Starting from the last few ns of the reported simulation during which the system tends to equilibrate, application of rare event sampling techniques becomes useful in taking the system away from the obtained minima by sampling other free-energy basins.

Figure 15A:
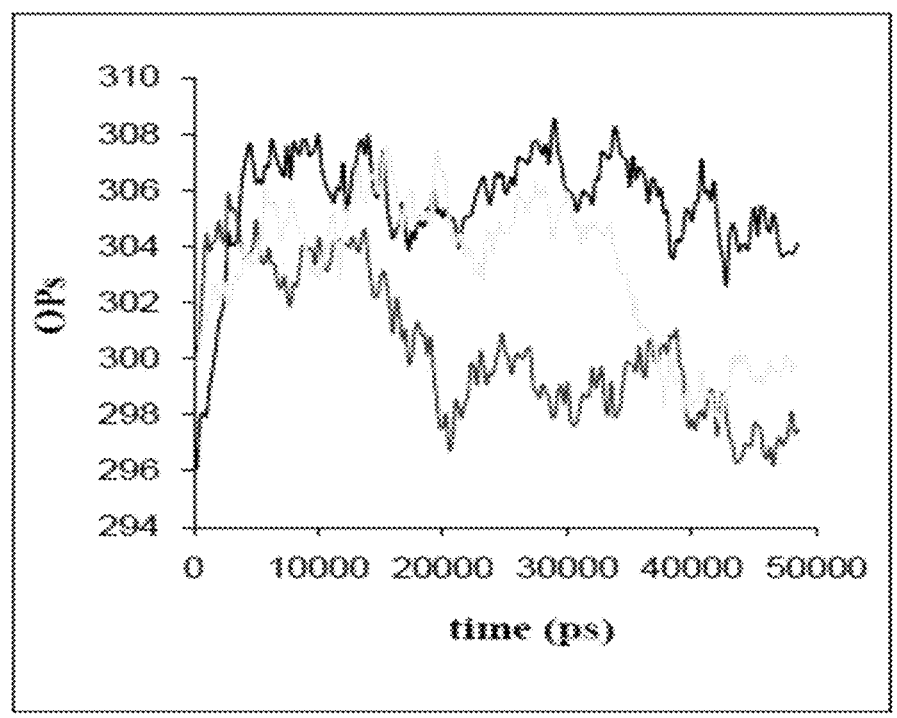
FIG. 15A is a diagram showing time evolution of the OPs for the protein bound RNA in 0.3M NaCl solution at 300K.
Figure 15B:
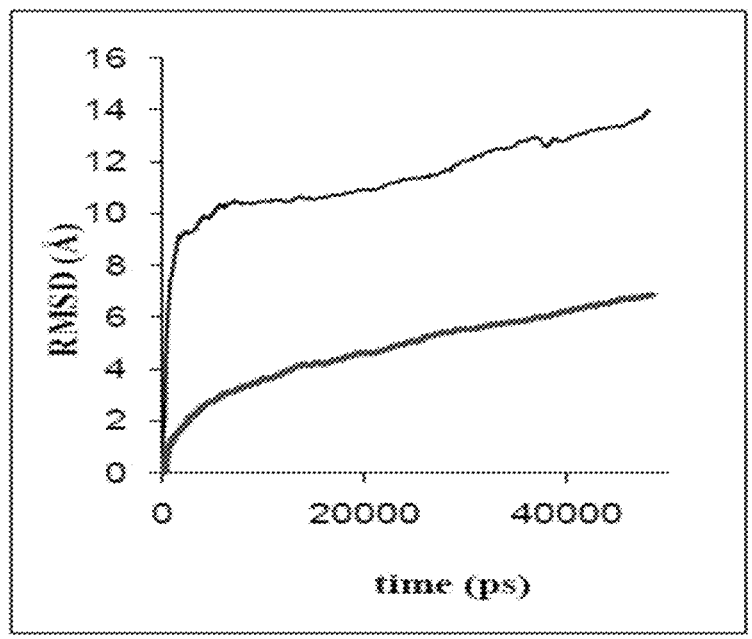
FIG. 15B is a diagram showing time evolution of the RMSD for the protein bound RNA in 0.3M NaCl solution at 300K.
Figure 15C:
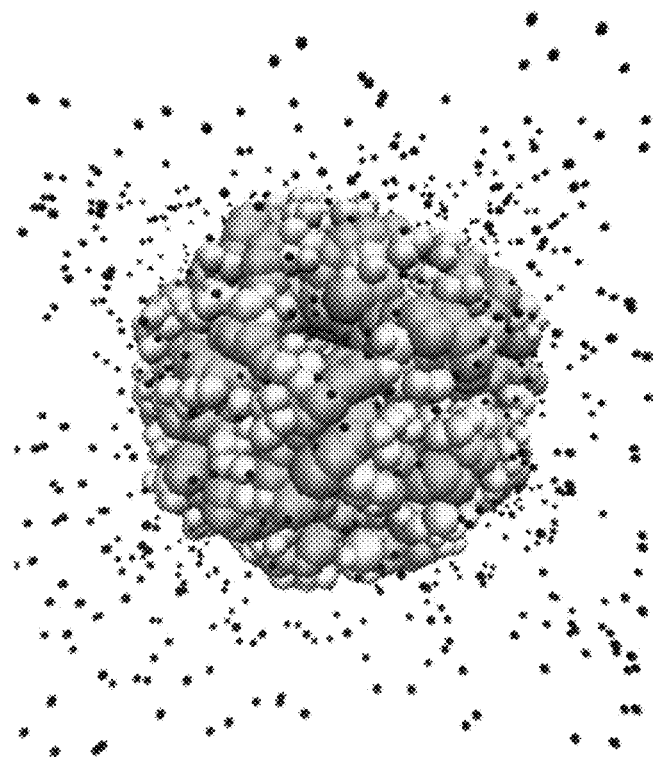
FIGS. 15C and 15D are depictions showing the structure for the protein bound RNA in 0.3M NaCl solution at 300K, showing the restriction on RNA motion imposed by the proteins.
Figure 15D:
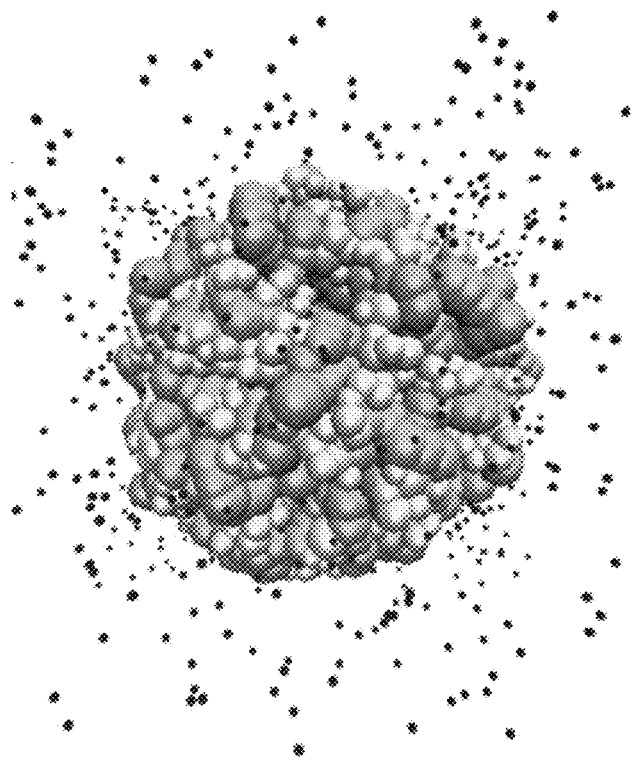

A control experiment was also performed to compare the deformation in the free RNA versus that in protein encapsulated RNA. The simulation was rerun using identical physical conditions (temperature, salinity) and software settings for the RNA core of STMV. The RNA core is composed of capsid protein strands (residue 2 to 27) complexed with the RNA. This complex is found to be stable with a radius distribution of ~50 Å. The added protein segments complex with the RNA, reducing the degrees of freedom. The structure was energy minimized and thermally equilibrated before starting the multiscale simulation. Time evolution of the OPs, the RMSD, and the structures for this simulation are shown in FIGS. 15A-D. FIG. 15B also shows the RMSD for free RNA. RMSD of RNA in the bound state is much less than in the free state. Unlike the previous case where the difference in the OPs was large, here the difference is small and their change is slower; this suggests the preservation of the symmetry originally imposed by the capsid. Thus, changes in the protein RNA complex are much less than those of free RNA. This longer characteristic time allows more efficient application of OP dynamics, as now timesteps of the order of 250 ps are possible. This implies that the presently disclosed software is 16 times faster than a single conventional MD for the present problem.

The simulations described above validate the presently disclosed efficient multiscale algorithm that probes the dynamics of macromolecules using OPs. The OPs are slowly varying and, hence, are well-suited as a basis of the multiscale algorithm. Completeness of a set of OPs may be determined by the shortness of correlation times relative to the characteristic time of OP evolution. Automated construction of order parameters enables efficient augmentation of the set of OPs to address incompleteness. The software simulation results show excellent agreement with those from a conventional MD run. The software simulation efficiency increases for larger systems undergoing slow transformations, as these allow significant length and timescale separation for the OPs to filter out the high frequency fluctuations from the coherent dynamics. Thus, OP mediated coarse-graining of the free-energy landscape allows for a Langevin timestep of a few hundred ps ($10^5$ times greater than conventional MD). The software simulation predictions correspond to an ensemble of MD trajectories and, hence, are more statistically significant than results from a single MD run. Multiscale simulation via the OP description was found to capture significant structural details like ion screening, hydrogen bond rearrangement and symmetry breaking transitions. In summary, the presently disclosed OP-multiscale computational approach is ideally suited for studying structural dynamics in large macromolecules and macromolecular complexes.

The present disclosure observes that variations in immunogenicity can exist between viral capsid protein assemblies of various sizes (e.g., between the L1 protein of HPV monomers, pentamers, and whole VLPs). These variations may be attributed to the intensity of fluctuations in epitope conformation for the various protein assemblies. The present disclosure validates this relationship between epitope fluctuation and immunogenicity for the illustrative embodiment of HPV L1 protein assemblies using molecular dynamics (MD) simulations. In the illustrative embodiment, epitope fluctuations were quantified via root-mean-square (RMS) deviation and features in the Fourier transform of dynamic changes in epitope structure. As epitope fluctuation affects immunogenicity (i.e., immune system recognition of an epitope may be more reliable when the epitope is presented via a more stable delivery structure), epitope fluctuation measurements can serve as one predictor of immunogenicity. As such, epitope fluctuation measurements may serve as part of computer-aided vaccine design methods.

As can be seen in FIG. 1, HPV VLPs look very much like the virus and are assembled out of 72 capsomers arranged on a T=7 icosahedral structure. The VLP surface has outwardly projecting loop regions that are recognized by the immune system triggering the production of antibodies specific to VLP type. Neutralizing antibodies bind to surface regions of the viruses spanning these different loops. Different HPV types produce different antibodies with varying immunogenic response and reactivity. Type specificity arises from the diversity of loop conformations in different HPV types even though the sequence homology between different HPV proteins is large. Neutralization assays of HPV16 VLPs with human sera have previously identified the following five epitope regions: BC (residues 49 to 70), DE (residues 110 to 154), EF (residues 170 to 189), FG (residues 262 to 291), and HI (residues 347 to 360).

These epitope regions, which are labeled in FIG. 1, are more flexible than the rest of the protein and contain sites for antibody binding. The FG and HI loops contain residues that bind to the monoclonal antibody H.16.V5, as previously observed in experiments in which loops transplanted from HPV16 VLPs to HPV11 proteins bind to H16.V5. H16.V5 binds strongly to VLPs containing FG and HI loops and weakly to VLPs having only the FG loop. Mutagenesis experiments, with deletion of certain H16.V5 epitopes mainly from residues in the HI loop and some in the FG loop, show that epitope-deleted VLPs are unaffected in their reactivity to human HPV sera—although their ability to bind H16.V5 is strongly reduced. However, epitope deletion reduces immunogenicity of these VLPs by a factor of at least 10 to 20 as compared to wild-type VLPs. Neutralization assays of human sera with HPV16 VLP epitopes show that the three loops DE, EF, FG are each essential for binding and that multiple regions on these loops contribute to antibody binding.

HPV pentamers are also viable vaccine candidates, as they form the units of the larger VLPs and automatically display the epitope regions of the whole VLP. HPV pentamers are significantly easier and more cost-efficient to produce than complete VLPs and, as stable particles with smaller size, are also easier to analyze and simulate. However, the pentameric unit is expected to behave differently from the whole VLP, which is expected to be more stable. The role of VLP assembly in epitope determination and stability also needs to be clarified before pentamers can be used as successful vaccines.

A structural study of HPV pentamers from different HPV types has shown differences in conformation and reactivity among them. However, X-ray data cannot adequately resolve loop regions and does not provide much information regarding the fluctuations of the loop regions. Based on X-ray crystallographic data, it has previously been concluded that overall pentamer conformation was almost the same within and outside the VLP, including the loop regions. However, the immunoglobulin density of HPV pentamer induces antibodies 20 to 40 times lower than those produced by the complete VLP. Binding assays of pentamer and VLP with different monoclonal antibodies show that VLPs are generally more reactive (as measured in absorption units). In the case of the monoclonal antibody H16.V5, the reactivity of the pentamer was only slightly lower than that of the VLP, but was much smaller in other cases. Both of these experimental observations suggest that there are important structural differences between VLPs and pentamers that have not been adequately resolved with X-ray data. The epitopes FG and HI are crucial for binding to H16.V5, with HI playing a major role. Therefore, the present disclosure examines the differences in the binding and immunogenicity of HPV pentamers, as compared to complete VLPs, using MD simulations of these systems.

The structural similarity of the epitope loop regions for the pentamer versus the VLP is believed to indicate that immunogenicity differences are related to the temporal variability in epitope loop conformation (i.e., fluctuation). As such, epitope fluctuation differences are related to differences of the forces exerted by the remainder of the structure. For example, a smaller assembly could be more highly fluctuating than a larger one due to differences in total assembly mass or flexibility of the assembly. The present disclosure reveals these differences in immunogenicity via MD simulations by measuring quantities that can distinguish atomic-level details in these systems. In other words, measurements of epitope fluctuation may serve as inputs to a quantitative structure-activity relationship (QSAR) vaccine design method, or to other vaccine design methods. Using epitope fluctuation measurements as inputs to a computer-aided vaccine design method may lead to more effective, thermally stable, and cost-effective vaccine delivery systems.

It is contemplated that the MD simulations used to determine epitope fluctuation measurements may be performed using any suitable simulation software. For instance, in some embodiments, MD simulations of protein assemblies may be performed using a deductive multiscale simulator, such as that described in PCT International Application No. PCT/US2012/020569, filed Jan. 7, 2012 (the entire disclosure of which is hereby incorporated by reference), in U.S. Provisional Patent Application No. 61/430,673, filed Jan. 7, 2011 (the entire disclosure of which is hereby incorporated by reference), and in Joshi et al., "Multiscale Simulation of Microbe Structure and Dynamics," 107 Progress in Biophysics & Molecular Biology 200-217 (2011) (the entire disclosure of which is hereby incorporated by reference). In the illustrative embodiment described below, the HPV16 (T=1) VLP, pentamer, and L1 protein were simulated separately under the same conditions to identify differences in structure and fluctuations in these systems. These illustrative simulations were run using the NAMD software program, with a TIP3 model for water and a particle mesh Ewald for calculating long-range electrostatic forces. Five nanoseconds of simulations were performed for the VLP, eight nanoseconds of simulations were performed for the HPV pentamer, and ten nanoseconds of simulations were performed for the L1 protein.

According to the illustrative embodiment, the following measurements of epitope fluctuation may be used, alone or in combination, to distinguish these systems: (1) distribution of backbone loop dihedral and side-chain dihedral angles in conformational space, (2) fluctuations of the loop atoms from their average value, (3) correlation analysis of the loops with each other and with regions that produce strong attractive or repulsive forces, and (4) power spectrum of the Fourier modes of the loop motions. The loop dihedral angles, their region of variation, and the fluctuations of the loop variables indicate the conformational space available to the epitopes. The magnitude of the fluctuations is a measure of the entropy of the loops and determines their flexibility. The correlation matrix provides a measure of the interactions between the different loops and provides additional information on important long-range forces exerted on loops that do not belong to the same protein. The Fourier spectral density gives the amplitude of wave-like motions of the loops.

FIGS. 2A, 2B, and 2C illustrate the regions of variation of the backbone dihedral angles for loop FG in the L1 protein, pentamer, and VLP, respectively. FIGS. 3A, 3B, and 3C illustrate the regions of variation of the backbone dihedral angles for loop HI in the L1 protein, pentamer, and VLP, respectively. One thousand data points were retained in each case from the simulations, making these plots a measure of probability distributions of loop conformations. As shown in FIGS. 2A-3C, loop HI maintains its native L1 conformation in pentamer and VLP, but loop FG occupies a smaller region in VLP compared to pentamer, and much smaller compared to its conformation in L1 protein. Loop FG's large flexibility in the protein appears diminished in pentamer and VLP. A structural analysis of the pentamer shows that loop HI from one pentamer is blanketed by loops EF and FG from its counterclockwise neighbor. Similarly, loop FG is blanketed by loops DE and HI from its clockwise neighbor. This arrangement leads to stronger interactions between loops FG and HI in pentamer and VLP than in L1 protein, where they are widely separated in space. The differences obtained in VLP and pentamer are also notable in loop FG. Loop BC is distant from other loops and projects out of the pentamer and VLP. As such, loop BC shows no significant differences in conformation between the three cases and most likely occupies a very wide conformational state. This result is expected, as this loop projects outward from the pentamer and is more mobile than the other loops that interact with adjacent loops. Unlike loop BC, loops DE and EF show minor differences in conformation. Loop DE is the longest of the loops and is expected to be more flexible than other loops. The beta sheet core that forms the L1 protein remains very stable in the pentamer and VLP, but appears to bend in the isolated protein in the region near loop HI. In summary, this conformational analysis of the loops yielded few major differences except for loop FG.

The overall fluctuation of a loop from its average position is a quantity not directly measurable in structure determination techniques like X-ray crystallography and cry-EM. While structural determination techniques provide the most likely or average location of a loop region, measurements of the fluctuation of a loop region indicate other important regions away from the average value. The loop fluctuation may be computed by summing the fluctuations of each individual backbone atom in the loop and then dividing by the total number of atoms. This measure is slightly different from usual RMS fluctuation, as it provides a measure of the entropy of the loop conformation (as opposed to RMS fluctuation that measures fluctuation from a fixed structure). The loop fluctuation is also sensitive to overall displacement of a loop, unlike RMS fluctuation that is normally calculated by aligning two structures (thereby eliminating any translational and rotational motions). The total fluctuations of each loop for VLP, L1 pentamer, and L1 protein are set forth below in Tables 1, 2, and 3, respectively, and more detailed plots of the fluctuations of individual loop backbone atoms are illustrated in FIGS. 4A-4C (for loop FG) and in FIGS. 5A-5C (for loop HI). The loop fluctuations for loops FG and HI are the largest in the protein, significantly smaller in the pentamer, and even smaller in the VLP. The fluctuations of loops BC, DE, and EF are not distinguishable between VLP and pentamer, but are much smaller than in the protein. The very large fluctuations seen in the L1 protein (even for loop HI, which does not sample newer conformations, as shown earlier) are due to overall displacement of loop atoms from the attached beta sheet.

TABLE 1

Loop fluctuations for VLP

| Loop | 2.5 ns | 5 ns |
| --- | --- | --- |
| BC | 2.9 | 4.4 |
| DE | 1.6 | 2.4 |
| EF | 3.5 | 5.3 |
| FG | 1.4 | 1.5 |
| HI | 2.8 | 3.0 |

TABLE 2

Loop fluctuations for L1 pentamer

| Loop | 4 ns | 8 ns |
| --- | --- | --- |
| BC | 2.1 | 3.5 |
| DE | 1.4 | 2.5 |
| EF | 3.2 | 5.4 |
| FG | 1.9 | 3.1 |
| HI | 2.7 | 4.3 |

TABLE 3

Loop fluctuations for L1 protein

| Loop | 5 ns | 10 ns |
| --- | --- | --- |
| BC | 5.4 | 16.2 |
| DE | 6.9 | 11.6 |
| EF | 12.4 | 17.3 |
| FG | 12.0 | 20.2 |
| HI | 21.9 | 51.6 |

The differences in loop fluctuations between the three systems are a result of complicated interactions between epitopes and proteins. Most of these interactions appear to be entropy determined and to not involve direct electrostatic forces. The loop interactions do not involve hydrogen bonds, as very few hydrogen bonds are formed with loop atoms. However, hydrogen bonds are formed between adjacent L1 in the pentamer in the core beta sheet region, making epitopes sensitive to backbone protein fluctuations. The complete VLP is further stabilized by the helix h4 posterior to the loop HI by interacting with helices h2 and h3 from pentamers related to it at points of three-fold symmetry. This interaction makes the pentamer in the VLP system less flexible and is a factor affecting stability of the epitopes. This interaction is also seen by comparing the spread between RMS deviations of pentamers and their individual proteins from their initial structure, with the spread being larger in pentamer than in VLP.

The extent of the correlation between loops and other regions can be compared in the pentamer and VLP systems by calculating the correlation matrix between important residues of the loop. This correlation analysis shows greater correlations between loops in VLP than in pentamer or protein.

The extent of motion of individual loop regions may be measured by RMS deviations from the initial structure for the VLP, pentamer, and L1 protein at the end of a simulation trajectory (e.g., 1 ns). The results of an illustrative simulation are presented below in Table 4. The last column of Table 4 compares structures obtained in the different loop regions for VLP and pentamer. The loop HI samples a well-defined conformation in the VLP and the pentamer, but moves away from its initial state in the L1 protein, suggesting strong interactions between this loop and neighboring monomers. The structures obtained at the end of the pentamer and VLP simulations have small deviation in the HI region. Loop FG, on the other hand, becomes more unstable from pentamer to L1 protein. The deviation of the structures obtained in VLP and pentamer simulations are also quite large for this loop. Tracking the deviation of the loops along a single trajectory indicates that they increase more in the pentamer than the VLP, except for loop HI that appears to change little in the two cases. The results of the simulation do not change significantly when the simulation is extended by another one nanosecond. The pentamer opens up after a long simulation, as measured by comparing the RMS deviation of an individual pentamer with the average RMS deviation of the five L1 proteins forming it.

TABLE 4

| RMS Deviation after 1 ns Simulation | | | | |
|---|---|---|---|---|
| Region | VLP | Pentamer | L1 | VLP/Pentamer |
| BC | .69 | 1.2 | 1.74 | 1.3 |
| DE | 1.63 | 1.37 | 1.56 | 2.2 |
| EF | .51 | 2.1 | 2.14 | 2.1 |
| FG | 1.1 | 1.55 | 2.56 | 2.3 |
| HI | .36 | .66 | 1.02 | 0.5 |

Summarizing the molecular dynamics, the L1 protein loop conformations are not very different from those in the bound pentamer and VLP, indicating that protein-protein interactions forming a pentamer and VLP do not induce any new conformations, but rather stabilize existing ones by restricting the motions of loops FG and HI. The loop fluctuation measurement, which is a measure of the entropy of the loop, shows a correlation between low entropy and higher immunogenicity. The loop HI is well defined and conserved in structure in the pentamer and VLP, whereas the loop FG is less conserved in the pentamer. This suggests inter-pentameric interactions stabilizing the conformation of loop FG and reducing the entropy of loop HI.

According to the present disclosure, MD simulations of HPV VLPs, pentamers, and L1 proteins show a correlation between the high immunogenicity observed for VLPs and the low entropy of loops FG and HI. This appears to be a result of differences in loop-loop and loop-protein interactions for the VLP versus the pentamer. Methods to minimize the entropy of loops FG and HI may lead to higher immunogenicity of VLP and pentamer based vaccines. This epitope fluctuation-immunogenicity relationship (validated herein for illustrative HPV L1 assemblies) may be applied to other viral systems, using epitope fluctuations as an input to a computer-aided vaccine design method. It will also be appreciated by those of skill in the art that even more reliable immunogenicity prediction may be achieved by combining an epitope fluctuation measure with other molecular descriptors.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure and the appended claims are desired to be protected.

APPENDIX A: LINEAR RELATIONSHIP BETWEEN OPS AND POSITIONS

The relationship between $\bar{\Phi}_k$ and $\bar{r}_i$ is taken here to be linear. This ensures that $\bar{r}_i$ has a unique value for a given set of $\bar{\Phi}_k$ and residuals (Eq. (2)). Should this not be the case then, as Newton's equations evolve $\underline{r}$, the system could spontaneously transition to another state of order without a change of microstate. By similar arguments application of $$\sum_{k'} B_{\underline{k}\underline{k}'} \vec{\Phi}_k = \sum_{i=1}^{N} m_i U_k(\vec{r}_i^o) \bar{g}(\vec{r}_i),$$

where $\bar{g}$ is a function of $\bar{r}_i$, may not always be suitable. This would have been implied by replacing Eq. (2) with $$\vec{g}(\vec{r}_i) = \sum_{k} \vec{\Phi}_k U_k(\vec{r}_i^o) + \vec{\sigma}_i.$$

If $\bar{g}$ is linear in $\bar{r}_i$, then the unique relation between $\bar{\Phi}_k$, residuals and $\bar{r}_i$ holds, allowing for the multiscale analysis presented above. However, if $\bar{g}$ is a nonlinear function of $\bar{r}_i$ then this uniqueness could be lost; multiple solutions for $\bar{r}_i$ could exist for a given set of $\bar{\Phi}_k$ and residuals. This could create situations wherein an initial $\underline{r}$ state evolves to multiple states allowed by the nonlinearity of $\bar{g}$. Newtonian mechanics prohibits this dynamical bifurcation of states (i.e., simultaneous evolution of one state into multiple ones); hence, in the present OP construction formalism, inclusion of a nonlinear function $\bar{g}$ could lead to unphysical results if uniqueness of the $\underline{r}$–$\underline{\Phi}$ relationship is violated. In other embodiments, other transformations may be designed that allow for nonlinear combinations of $\underline{r}$ without violating this uniqueness. The suggested bifurcation of states should not be confused with the multiplicity of atomic configurations that arise due to $\bar{\tau}_i$ sampling, as described above. The presently disclosed embodiment does not imply that the OP dynamics are linear, i.e., the thermal-average forces driving OP dynamics in general are related to the OPs in a highly nonlinear fashion. This nonlinearity is critical in simulating far-from equilibrium structures.

In the above context, Eq. (4) is the origin of the unique value of $\bar{\Phi}_k$ for a given set of $\bar{r}_i$. While $\underline{r}$ implies $\bar{\Phi}_k$ uniquely, the converse is not true, i.e., there is an ensemble of r for given $\underline{\Phi}$. This stems from the fact that a theory with $N_{OP}$(<<N) OPs cannot predict 3N atomic co-ordinates uniquely; this is the motivation for adding the residuals to Eq. (1) and generating an ensemble of atomic configurations consistent with the OPs (Eq. (2)). In particular, N $\bar{r}_i$ cannot be uniquely expressed in terms of $N_{OP}\bar{\Phi}_k$ from Eq. (3) or Eq. (4). Therefore, the $\underline{r}$–$\underline{\Phi}$ relationship is not one-to-one, as it should not be.

Generation of atomic ensemble consistent with coarse-grained variables has been discussed in other multiscale approaches. However, in these approaches the dynamics of all atoms was not accounted for, leading to issues in treating diffusion and long range electrostatics. One suggested way of overcoming this is to couple the atomistic and coarse-grained representations via the boundary conditions. This has been implemented by parameterization of a coarse-grained model with MD simulation data, and demonstrated on transmembrane proteins. In contrast, the presently disclosed approach accounts for the all-atom configurations via a quasi-equilibrium probability distribution which evolves adiabatically with the OPs. Visco-elastic effects in the dynamics of the macromolecule are accounted via thermal-average forces and diffusion coefficients.

APPENDIX B: DERIVATION OF THE MULTISCALE LIOUVILLE OPERATOR

The multiscale Liouville operator of Eq. (9) may be derived using the ansatz of Eq. (8) and the chain rule, starting from the classical Liouville operator L. The contribution to L$\rho$ from particle i is given by $$-\frac{\vec{p}_i}{m_i} \Box \frac{\partial \rho}{\partial \vec{r}_i} - \vec{F}_i \Box \frac{\partial \rho}{\partial \vec{p}_i} - \sum_{\alpha,\alpha',\underline{k}} \frac{p_{i\alpha}}{m_i} \left( \frac{\partial \Phi_{k\alpha'}}{\partial r_{i\alpha}} \right) \left( \frac{\partial \rho}{\partial \Phi_{k\alpha'}} \right)_{\Gamma=\Gamma_0}, \quad (17)$$

where $\alpha$ and $\alpha'$ signify Cartesian components of the position/momentum and Ops, respectively.

The first two terms in Eq. (17) are the $i^{th}$ contribution to $L_0$. Extending the above to N particles, $$L_0 = -\sum_{i=1}^{N} \left\{ \frac{\vec{p}_i}{m_i} \Box \frac{\partial}{\partial \vec{r}_i} + \vec{F}_i \Box \frac{\partial \rho}{\partial \vec{p}_i} \right\}. \quad (18)$$

Furthermore considering the third term of Eq. (17), the $\bar{\Phi}_k$–$\bar{r}$ relationship (Eq. (4)), and the definition of $\mu_{\underline{k}}$ (Eq. (6)) yields:

$$L_1 = \sum_{\underline{k}} \frac{\Pi_{\underline{k}}}{\mu_{\underline{k}}} \left( \frac{\partial \rho}{\partial \Phi_{\underline{k}}} \right)_{\Gamma=\Gamma_0}. \quad (19)$$

APPENDIX C: THERMAL-AVERAGE FORCES AS FREE-ENERGY GRADIENTS

By definition the $\alpha^{th}$ Cartesean component of the thermal-average force is given by $$f_{\underline{k}\alpha} = -\frac{\partial F}{\partial \Phi_{k\alpha}} = \frac{1}{\beta Q(\beta, \Phi)} \frac{\partial}{\partial \Phi_{k\alpha}} \int \omega d\Gamma^* \Delta(\underline{\Phi} - \underline{\Phi}^*) e^{-\beta H^*}, \quad (20)$$

where $\underline{\Phi}^*$ is the set of the first $N_{OP}$ components of $\underline{\Phi}^*_{ex}$ (i.e., $\underline{\Phi}_{ex}$ evaluated at $\Gamma^*$). The contribution $\tilde{Q}$ from the $\underline{r}^*$ integration of Eq. (20) is given by $$\tilde{Q} = \int \omega d^3 r^* \Delta(\underline{\Phi} - \underline{\Phi}^*) e^{-\beta H^*}. \quad (21)$$

As $\underline{\Phi}$ does not affect the momentum contribution to the Q-integral in deriving the thermal-average forces, one may proceed with the analysis of $\partial \tilde{Q}/\partial \Phi_{k\alpha}$.

It should be noted that the thermal averaging involves integration over all positions and momenta $\Gamma^*$, which are consistent with a given value of $\underline{\Phi}$ as imposed through the $\Delta$ factor. In taking the derivative of the integral with respect to $\Phi_{k\alpha}$, in concept, one calculates the integral at two closely lying $\Phi_{k\alpha}$ values and divides the difference by the increment in $\Phi_{k\alpha}$; at all stages of this conceptual calculation, H is taken to be a function of $\Gamma^*$ and not $\underline{\Phi}^*$ directly. This implies the $L_1H=0$ condition encountered in the course of constructing the multiple dependencies of $\rho_0$ is not violated.

Taking the derivative inside the integral in Eq. (20), and using the fact that $\Delta$ only depends on the difference $(\underline{\Phi}-\underline{\Phi}^*)$, one obtains:

$$\frac{\partial \tilde{Q}}{\partial \Phi_{k\alpha}^*} = -\int \omega d^3 r^* \frac{\partial \Delta(\underline{\Phi}-\underline{\Phi}^*)}{\partial \Phi_{k\alpha}^*} e^{-\beta H^*}. \tag{22}$$

Using Eq. (7) and the chain-rule yields:

$$\frac{\partial \tilde{Q}}{\partial \Phi_{k\alpha}^*} = -\int \omega d^3 r^* \sum_{\alpha'=1}^{3} \sum_{i=1}^{N} \frac{\partial \Delta(\underline{\Phi}-\underline{\Phi}^*)}{\partial r_{i\alpha'}^*} \frac{\partial r_{i\alpha'}^*}{\partial \Phi_{k\alpha}^*} e^{-\beta H^*} = \tag{23}$$

$$-\int \omega d^3 r^* \sum_{\alpha'=1}^{3} \sum_{i=1}^{N} \delta_{\alpha\alpha'} U_{\underline{k}}(\vec{r}_i^o) \frac{\partial \Delta(\underline{\Phi}-\underline{\Phi}^*)}{\partial r_{i\alpha'}^*} e^{-\beta H^*},$$

where Kronecker delta $\delta_{\alpha\alpha'}$ arises since $$\frac{\partial r_{i\alpha'}^*}{\partial \Phi_{k\alpha}^*}$$

is zero if $\alpha \neq \alpha'$. Integration by parts of Eq. (23), and simplification of the expression yield:

$$\frac{1}{\beta} \frac{\partial \tilde{Q}}{\partial \Phi_{k\alpha}^*} = \int \omega d^3 r^* \Delta(\underline{\Phi}-\underline{\Phi}^*) f_{\underline{k}\alpha}^{m^*} e^{-\beta H^*}, \tag{24}$$

where $$f_{\underline{k}\alpha}^{m^*} = \sum_{i} U_{\underline{k}}(\vec{r}_i^o) F_{i\alpha}^*, \text{ for } F_{i\alpha}^* = -\frac{\partial V^*}{\partial r_{i\alpha}^*}.$$

Here $V^*=V(\vec{r}^*_1, \vec{r}^*_2 \ldots \vec{r}^*_N)$ is the N-atom potential evaluated at $\underline{r}^*$.

Reinstating vector notation, integrating over the momenta, and dividing both sides by Q yields $$\vec{f}_{\underline{k}} = \frac{1}{Q} \int \omega d\Gamma^* \Delta(\underline{\Phi}-\underline{\Phi}^*) \vec{f}_{\underline{k}}^{m^*} e^{-\beta H^*} = \langle \vec{f}_{\underline{k}}^{m^*} \rangle. \tag{25}$$

This validates Eq. (14) and also shows how the interatomic forces $\vec{F}_i$ influence $\vec{f}_{\underline{k}}$ through the N-atom potential in H. In arriving at Eq. (25), all the position dependence of H is relegated to $\underline{r}^*$. Therefore, the condition $L_1H=0$ is sustained.

APPENDIX D: $\lambda$ COMPUTATION

Fluctuations $\lambda$ in SPs is calculated using:

$$\lambda(SP_j, t_i) = \frac{\sqrt{\sum_{i=0}^{N_f-1} [SP_j(t_i) - \langle SP_j \rangle]^2 / N_f}}{SP_{j,max}(t_i)};$$

$j=1, \ldots 4$, where $t_i$ is the $i^{th}$ time, $N_f$ is the total number of MD time frames used for the moving averages, $\langle SP_j \rangle$ is the moving average (over 50 ps), and $SP_{j,max}$ is the maximum absolute value of the SP within the range of SPs sampled for the moving average calculation. Fluctuations are defined about a moving absolute maxima rather than a moving average to avoid singularities for zero moving averages. The normalization makes $\lambda$ dimensionless. Thus $\lambda$ can be compared between different SPs and OPs.

What is claimed is:

1. A computer-aided vaccine design method comprising:
    performing, by a computer, one or more deductive multiscale molecular dynamics simulations of a protein assembly having at least one epitope using a plurality of order parameters, wherein the at least one epitope comprises a plurality of backbone atoms of a backbone of the protein assembly, wherein each of the plurality of order parameters describes a nanoscale feature of the protein assembly, wherein performing the one or more deductive multiscale molecular dynamics simulations comprises generating, at each time step of a plurality of time steps, an atomistic configuration of the protein assembly based on the plurality of order parameters;
    determining, by the computer, a fluctuation measurement for each of the plurality of backbone atoms of the at least one epitope using the one or more deductive multiscale molecular dynamics simulations; and
    predicting, by the computer, an immunogenicity of the protein assembly in response to the fluctuation measurements.

2. The computer-aided vaccine design method of claim 1, wherein the protein assembly is a virus-like particle.

3. The computer-aided vaccine design method of claim 1, wherein the protein assembly is a pentamer.

4. The computer-aided vaccine design method of claim 1, wherein determining the fluctuation measurement for each of the plurality of backbone atoms of the at least one epitope comprises determining a distribution of backbone dihedral angles in conformational space.

5. The computer-aided vaccine design method of claim 1, wherein determining the fluctuation measurement for each of the plurality of backbone atoms of the at least one epitope comprises calculating a root-mean-square deviation of epitope fluctuation.

6. The computer-aided vaccine design method of claim 5, wherein calculating the root-mean-square deviation of epitope fluctuation comprises summing fluctuations for each of the plurality of backbone atoms during the one or more deductive multiscale molecular dynamics simulations and dividing by a total number of the plurality of backbone atoms.

7. The computer-aided vaccine design method of claim 1, wherein determining the fluctuation measurement for each of the plurality of backbone atoms of the at least one epitope comprises calculating a correlation matrix between the at least one epitope and other structures in the protein assembly.

8. The computer-aided vaccine design method of claim 1, wherein predicting the immunogenicity of the protein assembly in response to the fluctuation measurement further comprises predicting the immunogenicity of the protein assembly in response to at least one other molecular descriptor of the protein assembly.

9. The computer-aided vaccine design method of claim 1, further comprising synthesizing a vaccine comprising the protein assembly.

10. The computer-aided vaccine design method of claim 1, wherein each time step of the plurality of time steps is between 1 and 100 picoseconds.

11. The computer-aided vaccine design method of claim 1, wherein performing the one or more deductive multiscale molecular dynamics simulations comprises updating, at each time step of the plurality of time steps, each of the plurality of order parameters based on the atomistic configuration of the protein assembly corresponding to the time step.

12. The computer-aided vaccine design method of claim 1, wherein performing the one or more deductive multiscale molecular dynamics simulations comprises:

(i) updating, by the computer, the atomistic configuration of the protein assembly based on the plurality of order parameters, wherein updating the atomistic configuration comprises determining a position for each of a plurality of atoms of the protein assembly;

(ii) simulating, by the computer and based on the atomistic configuration of the protein assembly, one or more interactions between the plurality of atoms;

(iii) updating, by the computer and based on the updated atomistic configuration of the protein assembly and the one or more simulated interactions between the plurality of atoms, each of the plurality of order parameters;

(iv) simulating, by the computer, a temporal evolution of the plurality of order parameters without use of the position of each of the plurality of atoms; and (v) repeating, by the computer, each of steps (i)-(iv) for each of the plurality of time steps of the deductive multiscale molecular dynamics simulation.

13. The computer-aided vaccine design method of claim 1, wherein each of the plurality of order parameters represents large-spatial-scale conformational changes and does not indicate high frequency atomic fluctuations.

14. One or more non-transitory, computer readable media comprising a plurality of instructions which, when executed by one or more processors, cause the one or more processors to:

perform one or more deductive multiscale molecular dynamics simulations of a protein assembly having at least one epitope with use of a plurality of order parameters, wherein the at least one epitope comprises a plurality of backbone atoms of a backbone of the protein assembly, wherein each of the plurality of order parameters describes a nanoscale feature of the protein assembly, and wherein to perform the one or more deductive multiscale molecular dynamics simulations comprises to generate, at each time step of a plurality of time steps, an atomistic configuration of the protein assembly based on the plurality of order parameters;

determine a fluctuation measurement for each of the plurality of backbone atoms of the at least one epitope using the one or more deductive multiscale molecular dynamics simulations; and predict an immunogenicity of the protein assembly in response to the fluctuation measurements.

15. The one or more non-transitory, computer readable media of claim 14, wherein the protein assembly is a virus-like particle.

16. The one or more non-transitory, computer readable media of claim 14, wherein the protein assembly is a pentamer.

17. The one or more non-transitory, computer readable media of claim 14, wherein the plurality of instructions cause the one or more processors to determine the fluctuation measurement for each of the plurality of backbone atoms of the at least one epitope, at least in part, by determining a distribution of backbone dihedral angles in conformational space.

18. The one or more non-transitory, computer readable media of claim 14, wherein the plurality of instructions cause the one or more processors to determine the fluctuation measurement for each of the plurality of backbone atoms of the at least one epitope, at least in part, by calculating a root-mean-square deviation of epitope fluctuation.

19. The one or more non-transitory, computer readable media of claim 18, wherein the plurality of instructions cause the one or more processors to calculate the root-mean-square deviation of epitope fluctuation by summing fluctuations for each of the plurality of backbone atoms during the one or more deductive multiscale molecular dynamics simulations and dividing by a total number of the plurality of backbone atoms.

20. The one or more non-transitory, computer readable media of claim 14, wherein the plurality of instructions cause the one or more processors to determine the fluctuation measurement for each of the plurality of backbone atoms of the at least one epitope, at least in part, by calculating a correlation matrix between the at least one epitope and other structures in the protein assembly.

21. A computer-aided vaccine design method comprising:

(i) determining, by a computer, a position of each of a plurality of atoms of an epitope of a protein assembly for a deductive multiscale molecular dynamics simulation;

(ii) simulating, by the computer and based on the position of each of the plurality of atoms, one or more interactions between the plurality of atoms;

(iii) determining, by the computer and based on the position of each of the plurality of atoms of the epitope and the one or more simulated interactions between the plurality of atoms, one or more order parameters for the deductive multiscale molecular dynamics simulation, wherein each of the one or more order parameters describes a nanoscale feature of the protein assembly;

(iv) simulating, by the computer, a temporal evolution of the one or more order parameters without use of the position of each of the plurality of atoms;

(v) updating, by the computer and based on the one or more updated order parameters, the position of each of the plurality of atoms of the epitope;

(vi) repeating, by the computer, each of steps (ii)-(v) for each of a plurality of time steps of the deductive multiscale molecular dynamics simulation;

(vii) determining, by the computer, a fluctuation measurement for each of the plurality of atoms of the epitope using the deductive multiscale molecular dynamics simulation; and (viii) predicting, by the computer, an immunogenicity of the protein assembly based on the fluctuation measurements.

\* \* \* \* \*